(12) United States Patent
Herzenberg et al.

(10) Patent No.: US 8,080,369 B2
(45) Date of Patent: Dec. 20, 2011

(54) METHODS FOR ACTIVATING PERIPHERAL BLOOD MONONUCLEAR CELLS (PBMCS) BY ADMINISTERING HUMAN IMMUNODEFICIENCY VIRUS (HIV) TAT UNDER PHYSIOLOGICAL OXYGEN LEVELS

(75) Inventors: Lenore A. Herzenberg, Stanford, CA (US); Bita Sahaf, Palo Alto, CA (US)

(73) Assignee: The Board of Trustees of the Leland Standford Junior University, Palo Alto, CA (US)

( * ) Notice: Subject to any disclaimer, the term of this patent is extended or adjusted under 35 U.S.C. 154(b) by 0 days.

(21) Appl. No.: 12/196,663

(22) Filed: Aug. 22, 2008

(65) Prior Publication Data

US 2009/0074813 A1 Mar. 19, 2009

Related U.S. Application Data

(60) Provisional application No. 60/957,335, filed on Aug. 22, 2007.

(51) Int. Cl.
*C12Q 1/70* (2006.01)
*G01N 33/00* (2006.01)
*A61K 39/21* (2006.01)

(52) U.S. Cl. ...... 435/5; 435/7.24; 424/188.1; 424/208.1

(58) Field of Classification Search .................. None
See application file for complete search history.

(56) References Cited

OTHER PUBLICATIONS

Hamy, F., et al., 1997, An inhibitor of the Tat/TAR RNA interaction that effectively suppresses HIV-1 replication, Proc. Natl. Acad. Sci. USA 94:3548-3553.*
HIV Sequence Compendium 2006/2007, Leitner T, Foley B, Hahn B, Marx P, McCutchan F, Mellors J, Wolinsky S, and Korber B, Eds., Published by Theoretical Biology and Biophysics Group, Los Alamos National Laboratory, NM, LA-UR 07-4826, pp. 588-589.*
Atkuri, K. R., et al., 2007, Importance of culturing primary lymphocytes at physiological oxygen levels, Proc. Nat. Acad. Sci. 104(11):4547-4552.*

* cited by examiner

*Primary Examiner* — Jeffrey S. Parkin
(74) *Attorney, Agent, or Firm* — Beverly W. Lubit; Greenberg Traurig, LLP

(57) ABSTRACT

The present invention relates to methods to activate peripheral blood mononuclear cells. The present invention further provides methods for the identification of blocking agents of Tat protein activation of PBMCs and for identifying an active portion of a Tat polypeptide for incorporation as an immunogen in a vaccine. The present invention also provides an immunogen comprising an isolated variant of wild-type HIV Tat protein that exhibits reduced HIV priming of competent cells in comparison to the wild-type HIV Tat protein. The present invention further provides a diagnostic kit for identifying blocking agents for HIV Tat protein.

13 Claims, 9 Drawing Sheets

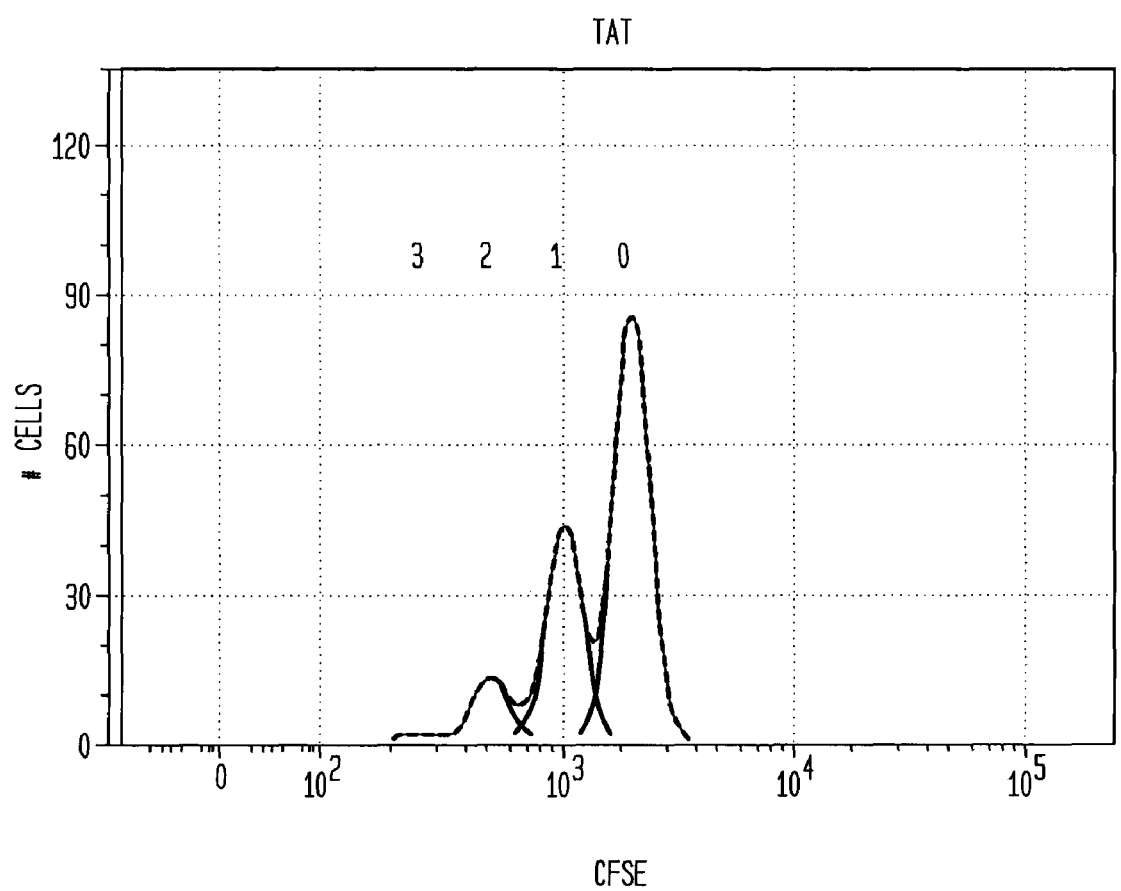

Figure 1:
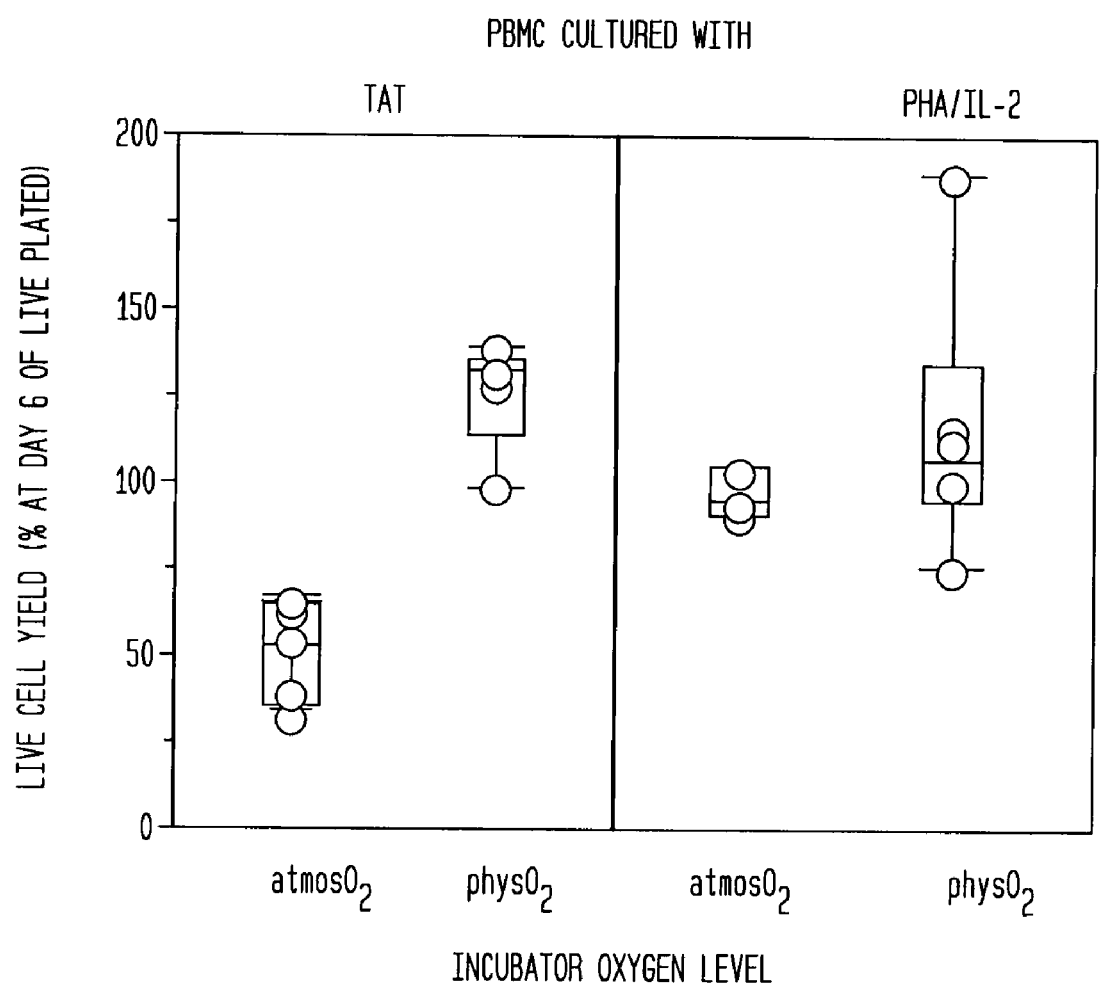

METHODS FOR ACTIVATING PERIPHERAL BLOOD MONONUCLEAR CELLS (PBMCS) BY ADMINISTERING HUMAN IMMUNODEFICIENCY VIRUS (HIV) TAT UNDER PHYSIOLOGICAL OXYGEN LEVELS

CROSS REFERENCE TO RELATED APPLICATIONS

This application claims the benefit of U.S. Patent Application 60/957,335, filed Aug. 22, 2007, incorporated by reference in its entirety herein.

FIELD OF THE INVENTION

The present invention relates to methods to activate peripheral blood mononuclear cells. The present invention further provides methods for the identification of blocking agents of Tat protein activation of PBMCs and for identifying an active portion of a Tat polypeptide for incorporation as an immunogen in a vaccine. The present invention also provides an immunogen comprising an isolated variant of wild-type HIV Tat protein that exhibits reduced HIV priming of competent cells in comparison to the wild-type HIV Tat protein. The present invention further provides a diagnostic kit for identifying blocking agents for HIV Tat protein.

BACKGROUND OF THE INVENTION

1. Transactivator of Transcription Protein (Tat)

The human immunodeficiency virus (HIV) transactivator of transcription (Tat) protein is a pleiotropic factor that induces a broad range of biological effects in numerous cell types. The Tat protein is encoded by two exons near the center of the viral genome. The first exon encodes amino acids 1 to 72, and the second exon encodes amino acids 73 to 101, although naturally occurring Tat sequences may be up to 113 amino acids long and the first exon may be up to 86 amino acids long. Studies have indicated an 86 amino acid version of Tat is sufficient for its transactivation function, which is necessary for virus transcription and replication in vitro; this form is the form most commonly used for research investigations, which have largely focused on in vitro studies of Tat as a transactivator of viral transcription, as an immunoregulator and an inducer of apoptosis. These studies have essentially all been conducted in vitro at atmospheric oxygen levels, which studies leading to the current invention have shown to dramatically alter human peripheral blood leukocyte response to Tat.

The Tat protein contains several functional subdomains. The amino terminus (1 to 20), cysteine-rich domain (21 to 40), and core region (1 to 48) together constitute the minimal activation domain for transcription in vitro. The N-terminal portion of Tat binds cell surface antigen CD26 with high affinity and has been reported to be responsible for CD26-mediated immunosuppressive activity. The cysteine-rich domain has homology to chemokines and mediates binding to chemokine receptors. The basic domain (also known as "shlepper"), characterized by a high content of lysines and arginines, is required for binding to short RNA transcripts containing the viral transactivation-response element. This basic domain is essential for importing extracellular Tat and also binds to membrane proteins, including the vascular endothelial growth factor receptor and heparan sulfate proteoglycans. Free peptide corresponding to the basic domain of Tat translocates through the cellular membrane and accumulates in the nucleus. The basic domain also may mediate toxin-like properties of Tat, including neuronal toxicity, and it appears to signal through cyclic nucleoside phosphodiesterase 4 to alter cyclic AMP levels. The function of the C terminus is still uncertain, but may be necessary for pathogenesis in vivo, since primary isolates express Tat of greater than 101 amino acids. The C termini of most Tat variants also contains an RGD motif that mediates Tat binding to cell surface integrins. The length of Tat varies depending on virus strain or lade (meaning a taxonomic group comprising a common ancestor and all the descendants of that ancestor).

2. Roles of Tat

The Tat protein is a critical component in the mechanism of AIDS pathogenesis. It is found in both the nucleus of infected cells, where it serves a conventional role in virus transcription, and as a secreted protein that can bind to the cell surface through electrostatic interactions, chemokine receptors, or cell surface integrins. Rapid uptake and importation of Tat into the nucleus occurs in many different cell types; however, some biological effects of Tat may require only membrane binding because they occur below the concentrations needed for transactivation of nuclear gene expression.

Tat protein is a key regulatory protein required for production of viral RNA and viral replication. The Tat protein of HIV is a powerful transactivator of gene expression. By interacting with a structured RNA sequence at the 5' end of the viral mRNA, it promotes the remodeling of chromatin and the recruitment of processive RNA polymerase complexes at the viral promoter. In addition to these transcriptional functions, a short amino acid motif (shlepper), highly enriched in basic amino acids (arginine rich domain), promotes the export of the protein from the expressing cells. Once in the extracellular environment, the same basic domain of Tat binds to cell surface heparan sulfate proteoglycans; apparently through this interaction, the protein is internalized by a variety of different cell types. Cellular internalization of Tat and Tat fusion proteins requires the integrity of cell membrane lipid rafts and mainly occurs through caveolar endocytosis. The Tat basic domain (shlepper), when attached to large protein cargos, also mediates efficient cellular internalization of these large protein cargos and thus can be utilized for transcellular protein transduction. This property already has been exploited successfully for the delivery of heterologous proteins, nanoparticles, liposomes, phage and viral vectors, and plasmid DNA. The biological significance of intercellular Tat trafficking in the context of viral infection still remains elusive.

Functional studies with Tat (summarized below) have largely been conducted in vitro, exclusively in standard incubators that are maintained in equilibrium with air (i.e., at atmospheric oxygen levels). Under these conditions, which are the current norm, the cells encounter oxygen levels well above the levels encountered in vivo (20% oxygen versus the 2% to 10% encountered in vivo). In addition, many of the studies conducted with Tat were conducted with long-established cell lines that have been grown exclusively at atmospheric oxygen levels and have lost many of the properties and sensitivities characteristic of peripheral blood mononuclear cells (PBMC) recently harvested from blood. In contrast, the studies that led to the current invention were conducted at physiological oxygen levels with freshly isolated PBMC, at which Tat behaves quite differently, e.g., it does not induce the extensive apoptosis that is induced at atmospheric oxygen levels. With this caveat, the summary below is presented.

Cell lines treated with Tat have shown increased expression of chemokine receptors, lower T-cell responses to antigenic stimulation, overproduction of interferon-α, and enhanced HIV replication due, it is thought, to increases in HIV transcriptional activation. Tat also has been shown to suppress mitogen-, alloantigen-, and antigen-induced lymphocyte proliferation in vitro by stimulating suppressive levels of interferon-α and/or by inducing extensive apoptosis. Tat may trigger apoptosis directly by induction of caspase pathways, or may increase expression of apoptosis inducing molecules (e.g., CD95 or TRAIL). Extracellular Tat also promotes T cell destruction (at atmospheric oxygen levels) by increasing expression of CD95L/Fas ligand on monocyte/macrophages and sensitizing cells to the effects of this molecule. CD95, also called Fas or APO-1, is a death receptor of the apoptotic mechanism and is expressed in activated T cells and NK cells. Other Tat studies have shown that there is an extensive loss of intracellular glutathione and production of ROS in Tat treated or transfected cells, perhaps due to Tat induction of oxidative stress (at atmospheric oxygen levels). Tat has been shown to facilitate Human Herpesvirus 8 ("HHV8") infection of epithelial cells that can host the virus. Tat also has been known to participate in vivo in the HHV8 infection that leads to the induction of Kaposi's Sarcoma, a tumor caused by HHV8. Further, Tat has been known to induce oxidative stress (a change in the normal redox state).

Many studies have demonstrated that Tat efficiently induces apoptosis in a wide variety of cells, including cultured peripheral blood mononuclear cells (PBMCs). These studies have been conducted in cells cultured in standard $CO_2$ (5%) incubators equilibrated with air (21% $O_2$). This has led to suggestions that Tat could play a role in the development of HIV-related neuropathies in vivo. In vivo, Tat may be taken up by neighboring cells. In vitro, Tat isolated from viral and recombinant sources has been shown to enter uninfected cells through a temperature dependent endocytic pathway, which originates from cell membrane lipid rafts and follows caveolar endocytosis. The arginine motif (shlepper or transducer motif) at amino acid positions 49 to 57 ($--_{49}$RKKRRQRRR$_{57}$--: SEQ ID NO: 3), which transports Tat into cells, is sufficient to also transport other proteins and molecules into PBMC and cell lines. Thus, this motif commonly is incorporated into constructs or otherwise coupled to macromolecules to enable their ready entry into cells. Full-length Tat also can function as a transporter, although such a use of Tat tends to induce substantial apoptosis under typical culture conditions.

Studies that led to the present invention began by demonstrating that Tat does not induce apoptosis in PBMC cultured at physiological oxygen levels. Instead, culturing PBMC at these oxygen levels induces cell division in a proportion of the cells and results in priming the cells for subsequently in vitro infection with HIV. These findings were interpreted as revealing a novel role for Tat in HIV disease, i.e., indicating that Tat released in vivo by HIV infected cells may prime neighboring cells for infection and hence facilitate the spread of the HIV infection, particularly at the early stages of the disease.

3. Tat Immunogens

Despite the growing knowledge of HIV disease progression, there remains a need in the art for development of compositions and methods of treatment of HIV, that could slow the spread of the virus and possibly prevent the onset of the subsequent AIDS disease.

The potential for therapeutic or preventive immunization with Tat protein has been the subject of animal and clinical studies. Development of vaccines against Tat may allow for control of its toxic properties. Immunization studies in animals involving biologically active Tat or recombinant vaccinia vectors expressing Tat and Rev (anti-repression transactivator protein) proteins have shown lower virus burden after challenge. In addition, the presence of anti-Tat serum antibodies or Tat-specific cytotoxic lymphocyte responses have been correlated with slow progression in HIV-infected individuals. However, the potential value of Tat as a vaccine antigen is controversial. Studies indicating complete or partial protection against viral challenge in macaques contrast with studies showing no protection. One study reported that therapeutic immunization with chemically inactivated Tat toxoid elicited strong immune responses in human beings that may be associated with clinical improvement. Other studies have shown that effective immunization with Tat toxoid failed to protect against mucosal transmission but did attenuate virus replication and disease. But although immunization was effective in protecting against disease, it did not provide sterilizing immunity against virus transmission. Response to immunization have been variable, but among animals with both cellular and humoral responses to Tat, studies have shown 88% were protected against disease progression.

Studies have indicated that Tat vaccines and, especially, formulations containing native Tat will not be effective as preventive, monovalent vaccines against HIV infection.

Additional studies utilizing modified inactive forms of the protein (Tat toxoid) via carboxymethylation of cysteine residues have been performed. Immunization studies with Tat or Tat toxoid have shown significant Tat-binding antibody titers and disease attenuation, although no animals were protected from infection. No statistically significant differences in disease among animals immunized with Tat or Tat toxoid in terms of viral RNA levels or CD4 cell counts were observed, although the Tat-immunized group tended to have lower viral RNA levels at set point compared with the Tat toxoid-immunized animals.

Studies utilizing monoclonal antibodies against the amino acid terminus or the domain RPPQ sequence have blocked Tat uptake into T cells and neutralized Tat in cell-based transactivation assays.

Several studies have focused on the role Tat plays in the immunopathogenesis of HIV, predicting that high-affinity neutralizing antibodies against Tat will improve the clinical prognosis of HIV infected patients. Epidemiological studies have observed an inverse relationship between the level of Tat-specific serum antibodies and the rate of disease progression. Studies indicate that the development of a highly effective Tat vaccine will depend on the identification of an appropriate Tat vaccine formulation that induces immune responses that completely block the immune-modulating activity of Tat.

HIV-1 Tat and Tat toxoid proteins are highly immunogenic in macaques and humans. Modified forms of Tat, including Tat toxoid, have been designed to avoid potential toxic effects of the protein. Studies have shown that these modifications restrict the pattern of antibody responses and elicit type-specific antibodies in macaques that do not recognize all Tat sequences equally. Thus, in order to study the response to Tat during infection or to develop broadly cross-reacting Tat vaccines, it is important to use sequences commonly present in the target population or to develop a mixture of antigens that overcomes the problem of sequence specificity.

Although animal models have been utilized to investigate Tat vaccine formulations, non-animal models are needed to accelerate the development of improved Tat vaccine formulations. The present invention addresses this need for non-animal models that allow design and pre-clinical assessment of HIV Tat vaccines.

Since Tat can prime cells for HIV infection under physiological conditions, monoclonal antibodies or other agents that can prevent Tat entry into cells or otherwise prevent Tat priming for HIV infection could be useful for slowing the progress of HIV disease.

To date, binding agents directed to the Tat molecule have proved unsuccessful in preventing entry of Tat into a cell. The present invention addresses this problem. It is based on the principle that, in order to prevent Tat priming, a binding agent, must block appropriate site(s) on the Tat molecule, and provides compositions and methods to identify such binding agents. The binding agents so identified may be used to identify targets on the Tat sequence that in turn may be used to produce vaccines that stimulate Tat inhibitory activity.

SUMMARY OF THE INVENTION

The present invention relates to methods to activate peripheral blood mononuclear cells. The present invention further provides methods for the identification of blocking agents of Tat protein activation of PBMCs and for identifying an active portion of a Tat polypeptide for incorporation as an immunogen in a vaccine. The present invention also provides an immunogen comprising an isolated variant of wild-type HIV Tat protein that exhibits reduced HIV priming of competent cells in comparison to the wild-type HIV Tat protein. The present invention further provides a diagnostic kit for identifying blocking agents for HIV Tat protein.

According to one aspect, the present invention provides a method to activate peripheral blood mononuclear cells, the method comprising the steps: (a) administering wild-type Tat protein to a cell culture, the cell culture comprising cells, wherein the cells are peripheral blood mononuclear cells; (b) maintaining the cell culture at physiological oxygen levels; (c) activating the cells of the cell culture; and (d) obtaining a population of phenotypically converted activated peripheral blood mononuclear cells. According to one embodiment, the cells of step (a) are non-HIV infected cells. According to another embodiment, the activated cells of step (c) have a memory T-cell phenotype. According to another embodiment, the activated cells of step (c) have at least one biomarker of the phenotype $CD45Ro^{(+)}$, $CD95^{(+)}$, and $CD45RA^{(-)}$. According to another embodiment, the activated cells of step (c) have a CD3 dull phenotype by flow cytometry. According to another embodiment, the population of phenotypically converted peripheral blood mononuclear cells constitutes at least about 20% of the cell population.

According to another embodiment, the cell culture is maintained at about 5% oxygen. According to another embodiment, the wild-type HIV Tat protein is of an amount sufficient for activation of peripheral blood mononuclear cells. According to another embodiment, the Tat protein is provided in amounts from about 1 ng/ml to about 100 n/ml. According to another embodiment, the Tat protein has a polypeptide sequence of substantial similarity to the polypeptide sequence [SEQ ID NO: 1], wherein the wild-type HIV Tat protein further comprises a conserved segment, wherein the conserved segment is of the formula: X1-X2-X3-X4-X5-X6-X7-X8-X9-X10-X11-X12-X13-X14-X15-X16-X17-X18-X19-X20 [SEQ ID NO: 12], wherein X1 is A; X2 is C, X3 is T; X4 is N; X5 is C; X6 is Y; X7 is C; X8 is K; X9 is K; X10 is C; X11 is C; X12 is F; X13 is H; X14 is C; X15 is Q; X16 is V; X17 is C; X18 is F; X19 is I; and X20 is T. According to another embodiment, the Tat protein is a recombinant protein.

According to another aspect, the present invention provides a method for the identification of blocking agents of Tat protein activation of peripheral blood mononuclear cells, the method comprising the steps: (a) providing a cell culture, the cell culture comprising cells, wherein the cells are peripheral blood mononuclear cells; (b) administering wild-type HIV Tat protein to the cell culture; (c) administering a blocking agent to the cell culture; and (d) maintaining the cell culture at physiological oxygen levels; wherein the blocking agent associates with an active portion of the Tat protein, thereby preventing a phenotypic conversion of the peripheral blood mononuclear cell population. According to one embodiment, the cell culture is maintained at about 5% oxygen. According to another embodiment, the wild-type HIV Tat protein is of an amount sufficient for activation of peripheral blood mononuclear cells. According to another embodiment, the Tat protein is provided in amounts from about 1 ng/ml to about 100 lag/ml. According to another embodiment, the Tat protein has a polypeptide sequence of substantial similarity to the polypeptide sequence [SEQ ID NO: 1], wherein the wild-type HIV Tat protein further comprises a conserved segment, wherein the conserved segment is of the formula: X1-X2-X3-X4-X5-X6-X7-X8-X9-X10-X11-X12-X13-X14-X15-X16-X17-X18-X19-X20 [SEQ ID NO: 12], wherein X1 is A; X2 is C, X3 is T; X4 is N; X5 is C.; X6 is Y; X7 is C; X8 is K; X9 is K; X10 is C; X11 is C; X12 is F; X13 is H; X14 is C; X15 is Q; X16 is V; X17 is C; X18 is F; X10 is 1; and X20 is T. According to another embodiment, the Tat protein is a recombinant protein. According to another embodiment, the active portion is the conserved segment. According to another embodiment, the blocking agent is an inhibitor. According to another embodiment, the blocking agent is an antagonist. According to another embodiment, the blocking agent is an agonist. According to another embodiment, the blocking agent is an antibody. According to another embodiment, the blocking agent is an antibody fragment that specifically binds to at least a segment of a polypeptide substantially similar to [SEQ ID NO: 1].

According to another aspect, the present invention provides a method for identifying an active portion of a Tat polypeptide for incorporation as an immunogen in a vaccine, the method comprising the steps: (a) providing a cell culture, the cell culture comprising cells, wherein the cells are peripheral blood mononuclear cells; (b) maintaining the cell culture at physiological oxygen levels; (c) administering Tat polypeptide to the cell culture; (d) administering a blocking agent to the cell culture; wherein the blocking agent associates with an active portion of the Tat polypeptide such that Tat polypeptide activity is reduced; (e) isolating the segment of the Tat polypeptide that specifically associates with the blocking agent, wherein the segment comprises the active portion; and (f) incorporating the active portion of step (e) into a vaccine; whereby the vaccine elicits an immunogenic response to the Tat active portion. According to one embodiment, the Tat protein is a wild-type HIV Tat protein. According to another embodiment, the Tat protein has a polypeptide sequence of substantial similarity to the polypeptide sequence [SEQ ID NO: 1]. According to another embodiment, the cell culture is maintained at about 5% oxygen. According to another embodiment, the Tat protein is of an amount sufficient for activation of peripheral blood mononuclear cells. According to another embodiment, the Tat protein is provided in amounts from about 1 ng/ml to about 100 µg/ml. According to another embodiment, the vaccine further comprises an adjuvant.

According to another aspect, the present invention provides an immunogen comprising an isolated variant of wild-type HIV Tat protein, wherein the isolated variant has a polypeptide sequence of substantial identity to [SEQ ID NO: 1], wherein the isolated variant further comprises a conserved segment, wherein the conserved segment is of the formula: X1-X2-X3-X4-X5-X6-X7-X8-X9-X10-X11-X12-X13-X14-X15-X16-X17-X18-X19-X20 [SEQ ID NO: 11 ], wherein X1 is A; X2 is C or S; X3 is T; X4 is N; X5 is C or S;

X6 is Y; X7 is C or S; X8 is K; X9 is K; X10 is C or S; X11 is C or S; X12 is F; X13 is H; X14 is C or S; X15 is Q; X16 is V; X17 is C or S; X18 is F; X19 is I; X20 is T; wherein at least one of X2, X5, X7, X10, X11, X14 and X17 is S; and wherein the isolated variant exhibits reduced HIV priming of competent cells in comparison to the wild-type HIV Tat protein.

According to another aspect, the present invention provides a diagnostic kit for identifying blocking agents for HIV Tat protein, the kit comprising components: (a) a cell population comprising peripheral blood mononuclear cells; wherein the cell population is maintained in a $CO_2$ incubator at about 5% oxygen; (b) a stimulating agent having a polypeptide sequence substantially similar to [SEQ ID NO: 1]; (c) a putative blocking agent; and (d) a means for admixing component (a), component (b), and component (c); wherein the blocking agent associates with the stimulating agent of component (b), thereby preventing stimulating agent activation of the cell population of component (a). According to one embodiment, the stimulating agent is Tat. According to another embodiment, the stimulating agent is of an amount sufficient for activation of peripheral blood mononuclear cells. According to another embodiment, the stimulating agent is provided in amounts from about 1 ng/ml to about 100 μg/ml. According to another embodiment, the blocking agent is an inhibitor. According to another embodiment, the blocking agent is an antagonist. According to another embodiment, the blocking agent is an agonist. According to another embodiment, the kit further provides component (e): a means of analyzing the cells within component (d). According to another embodiment, the means of analyzing the cells within component (d) is flow cytometry.

BRIEF DESCRIPTION OF THE DRAWINGS

FIG. 1 shows that Tat induction of apoptosis is extensive in PBMC cultured at atmospheric oxygen levels (20% $O_2$), but is minimal at physiological oxygen levels (5% $O_2$). PBMCs ($10^6$/ml) were cultured with Tat or PHA/IL-2 (2-5 μg/ml; 50 Units/ml) at atmospheric oxygen levels (right panel) or physiological oxygen levels (left panel).

FIG. 2 shows that Tat induces proliferation of PBMCs cultured at physiological oxygen levels ($PhysO_2$). PBMCs were labeled with 0.5 μM CFSE (CarboxyFluorescein DiAcetate Succinimidyl-Ester, CFDA) for 10 minutes at 37° C. and then cultured for 6 days with Tat or IL-2/PHA as indicated to evaluate cell division during the culture period. Each cell division decreases the amount of CFSE detected per cell by half. Dashed curves show the computed frequencies of cells that have undergone the indicated number of cell divisions.

FIGS. 3A and 3B show that Tat rapidly enters PBMCs. PBMCs mixed with Tat labeled with AlexaFluor488 were incubated either at 37° C. at $physO_2$ (FIG. 3A) or kept on ice for the indicated time period. PBMC were incubated with Tat-AlexaFluor for 2 hours at 37° C. at $physO_2$. For FACS studies (FIG. 3A), cells were stained at 4° C. after incubation with Tat. Viable lymphocytes were further gated to reveal the indicated subsets. "Fluorescence-minus-one" (FMO) controls reveal fluorescence detected in the Tat channel for cells that were not incubated with Tat but were stained with all other reagents (lower panels).

FIG. 4 shows that Tat efficiently primes PBMCs for HIV infection and supports viral production by the infected cells. The right panel shows that Tat is equivalent to PHA/IL-2 for priming and is equivalent to IL-2 for support of HIV infection. PBMC were maintained for 3 hours at 5% oxygen throughout the experiment. PBMC were infected with HIV-1 (LAI) for 3 hours after priming. HIV p24 was measured in supernatants by ELISA.

FIG. 5 shows that Tat primes PBMCs for HIV infection within about 2 hours. (*)=At 3 days, there is roughly a 2-4 fold increase in the number of cells in the culture and hence in the number of cells that were infected and allowed to produce virus during the 6 day support phase.

FIG. 6 shows that mutating the seven Cysteine (Cys) residues in wild-type TAT to Serine (Ser) destroys Tat priming of cells for HIV infection. A p24 ELISA was used to determine the levels of the HIV-core p24 produced by infected cells after treatment with native Tat and Tat variants Cys31 Ser, Cys22, 25, 27, 30, 31, 34, 37Ser. PBMCs were primed using PHA/IL2. IL2 was used to support the infection. PBMC treated as indicated for 72 hours and then infected with HIV-1 (LAI) for 3 hours, at 5% oxygen. Infected cells were then cultured for another 6 days in RPMI media supplemented with IL-2. Secreted p24 was measured in the supernatant using ELISA.

FIG. 7. PBMC cultured 3 hours with Tat stimulates the appearance of a "new" T cell subset. The new subset is characterized by low levels of CD3 in the Tat stimulated cultures (upper panel). Gating on the dull CD3+ cells reveals a CD62L-bright subset that is present in the Tat-stimulated culture but is not detectable in the comparably gated control.

DETAILED DESCRIPTION OF THE INVENTION

The present invention provides methods for activation of peripheral blood mononuclear cells (PBMCs). The present invention further provides methods for the identification of blocking agents that prevent Tat polypeptide activation of PBMCs. The present invention also provides methods for identifying an active portion of a Tat polypeptide for incorporation as an immunogen in a vaccine and provides isolated immunogens thereof.

Definitions

The term "attenuate" as used herein refers to render less virulent, to weaken or reduce in force, intensity, effect or quantity.

The term "minimizing progression" as used herein refers to reducing the amount, extent, size, or degree of development of a sequence or series of events.

The term "reduced" or "to reduce" as used herein refer to a diminish, a decrease, an attenuation or abatement of the degree, intensity, extent, size, amount, density or number of.

The term "prime" (or "priming") as used herein refers the process of increasing sensitivity to. When used in an immunological sense it refers to a process whereby a specific antigen is presented to naïve lymphocytes causing them to differentiate.

The term "support" is used herein to refer to sustain, supply, maintain, assist, or to provide for allowing viral infection to proceed and virus to be produced.

The term "PHA/IL-2" is used herein to refer to a mitogen (phytohemagglutinin)/cytokine (interleukin-2) combination for priming and support of HIV infection. The term "mitogen" as used herein refers to any substance or agent that stimulates mitotic cell division.

The term "cell" is used herein to refer to the structural and functional unit of living organisms and is the smallest unit of an organism classified as living. As used herein, cells may refer to, but are not limited to, cells of a mammal, human, hamster, rodent, dog, cat, rabbit, goat, red blood cells, peripheral blood mononuclear cells, cells of the human immune system, including, leukocytes, white blood cells, phagocytes, macrophages, neutrophils, dendritic cells, mast cells, eosinophils, basophils, natural killer cells, monocytes, lymphocytes, B cells, T cells, killer T cells, helper T cells, γδ T cells, plasma cells, epithelial cells, neuronal cells, sperm cells, or cells commonly used in tissue culture such as, for example, HeLa, and the like.

The terms "peripheral blood mononuclear cells" or "PBMCs" are used interchangeably herein to refer to blood cells having a single round nucleus such as, for example, a lymphocyte or a monocyte. PBMCs are a critical component in the immune system's responses to infections.

The term "peptide" is used herein to refer to two or more amino acids joined by a peptide bond.

The term "polypeptide" is used herein to refer to a peptide containing about 10 to more than about 100 amino acids.

The term "protein" is used herein to refer to a large complex molecule or polypeptide composed of amino acids. The sequence of the amino acids in the protein is determined by the sequence of the bases in the nucleic acid sequence that encodes it.

The terms "peptide", "polypeptide" and "protein" also apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well.

The terms "vector" and "expression vector" are used herein to refer to a replicon, i.e., any agent that acts as a carrier or transporter, such as a phage, plasmid, cosmid, bacmid, phage or virus, to which another genetic sequence or element (either DNA or RNA) may be attached so as to bring about the replication of the attached sequence or element and so that sequence or element can be conveyed into a host cell.

The term "wild-type HIV Tat protein" are used herein to refers to an isolated polypeptide having an amino acid sequence corresponding to the amino acid sequence of a naturally occurring HIV Tat protein. A wild-type HIV Tat protein is a protein having, or having substantial similarity to, the amino acid sequence of MEPVDPRLEP WKHPG-SQPKT ACTNCYCKKC CFHCQVCFIT KALGISYGRK KRRQRRRAHQ NSQTHQASLS KQPTSQPRGD PTGP-KEXKKK VERETETDPF [SEQ ID NO: 1]. One skilled in the art will readily recognize that amino acid sequences of wild-type HIVTat proteins differ nonsubstantially in length and composition amongst different strains and clades of HIV virus and that wild-type HIV Tat protein amino acid sequences comprise at least one segment of conserved amino acids. These segments of conserved amino acids include, but are not limited to, ACTNCYCKKCCFHCQVCFIT [SEQ ID NO: 2] (corresponding, for example, to amino acid position 21 through position 40 of [SEQ ID NO: 1]) and RKKRRQRRR [SEQ ID NO: 3] (corresponding, for example, to amino acid position 49 through position 57 of [SEQ ID NO: 1], referred to as "shlepper"). As described herein, the amino acid residue substitutions of the isolated variants typically are found within the conserved segment [SEQ ID NO: 2] within the wild-type HIV Tat protein polypeptide sequence [SEQ ID NO: 1], or substantially similar sequences thereof.

The term "conserved segment" is used herein to refer to similar or identical sequences that may occur within nucleic acids, proteins or polymeric carbohydrates within multiple species of organism or within different molecules produced by the same organism.

The term "variant of wild-type HIV Tat protein" is used herein to refer to a wild-type HIV polypeptide sequence in which at least one amino acid residue has been modified by deletion of an amino acid, insertion of an amino acid, or substitution of a second amino acid for a first amino acid at a specific position on the polypeptide.

The terms "residue" or "amino acid residue" or "amino acid" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids.

The terms "variants", "mutants", and "derivatives" are used herein to refer to nucleotide sequences with substantial identity to a reference nucleotide sequence. The differences in the sequences may by the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence.

A skilled artisan likewise can produce polypeptide variants having single or multiple amino acid substitutions, deletions, additions or replacements. These variants may include inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (d) variants in which a target protein is fused with another peptide or polypeptide such as a fusion partner, a protein tag or other chemical moiety, that may confer useful properties to the target protein, such as, for example, an epitope for an antibody. The techniques for obtaining such variants, including genetic (suppressions, deletions, mutations, etc.), chemical, and enzymatic techniques are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "substitution" is used herein to refer to that in which a base or bases are exchanged for another base or bases in the DNA. Substitutions may be synonymous substitutions or nonsynonymous substitutions. As used herein, "synonymous substitutions" refer to substitutions of one base for another in an exon of a gene coding for a protein, such that the amino acid sequence produced is not modified. The term "nonsynonymous substitutions" as used herein refer to substitutions of one base for another in an exon of a gene coding for a protein, such that the amino acid sequence produced is modified.

The terms "deletion" and "deletion mutation" are used interchangeably herein to refer to that in which a base or bases are lost from the DNA.

The term "addition" as used herein refers to the insertion of one or more bases, or of one or more amino acids, into a sequence.

The following represent groups of amino acids that are conservative substitutions for one another:
1) Alanine (A), Serine (S), Threonine (T);
2) Aspartic Acid (D), Glutamic Acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "similar" is used interchangeably with the terms analogous, comparable, or resembling, meaning having traits or characteristics in common.

The term "stimulate" as used herein refers to activate, provoke, or spur. The term "stimulating agent" as used herein refers to a substance that exerts some force or effect.

The term "subject" or "individual" or "patient" are used interchangeably to refer to a member of an animal species of mammalian origin, including but not limited to, mouse, rat, cat, goat, sheep, horse, hamster, ferret, pig, dog, platypus, guinea pig, rabbit and a primate, such as, for example, a monkey, ape, or human.

The term "pharmaceutical composition" is used herein to refer to a composition that is employed to prevent, reduce in intensity, cure or otherwise treat a target condition or disease.

The term "prevent" as used herein refers to effectual stoppage of action or progress.

The term "multiplication" as used herein refers to an increase or growth in number, amount, or degree.

The terms "inhibiting", "inhibit" or "inhibition" are used herein to refer to reducing the amount or rate of a process, to stopping the process entirely, or to decreasing, limiting, or blocking the action or function thereof. Inhibition may include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "nucleic acid" is used herein to refer to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" is used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity".

The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software performing BLAST analyses is publicly available, e.g., through the National Center for Biotechnology-Information at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer l-ISPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, and expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) Proc. Natl. Acad, Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters may be employed alone or in combination.

The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The terms "substantial identity" in the context of a peptide indicates that a peptide comprises a sequence with at least 70% sequence identity to a reference sequence, at least 80%, at least 85%, at least 90% or 95% sequence identity to the reference sequence over a specified comparison window. Optionally, optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

The term "isolated" is used herein to refer to material, such as, but not limited to, a nucleic acid, peptide, polypeptide, or protein, which is: (1) substantially or essentially free from components that normally accompany or interact with it as found in its naturally occurring environment. The terms "substantially free" or "essentially free" are used herein to refer to considerably or significantly free of, or more than about 95% free of, or more than about 99% free of. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state. For example, a naturally occurring nucleic acid becomes an isolated nucleic acid if it is altered, or if it is transcribed from DNA that has been altered, by means of human intervention performed within the cell from which it originates. See, for example, Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (for example, a promoter) becomes isolated if it is introduced by non-naturally occurring means to a locus of the genome not native to that nucleic acid. Nucleic acids that are "isolated" as defined herein also are referred to as "heterologous" nucleic acids.

The term "marker" is used herein to refer to a receptor, or a combination of receptors, found on the surface of a cell. These markers allow a cell type to be distinguishable from other kinds of cells. Specialized protein receptors (markers) that have the capability of selectively binding or adhering to other signaling molecules coat the surface of every cell in the body. Cells use these receptors and the molecules that bind to them as a way of communicating with other cells and to carry out their proper function in the body. Several markers include, but are not limited to, Ro (an autoantigen that likely functions in a quality control pathway for defective noncoding RNAs); CD95 (or Apo-1; a cell surface receptor triggers a cascade of signaling events, including assembly of the death-inducing signaling complex (DISC), that culminate in cellular apoptosis); and RA (retinoic acid receptor, RA is the bioactive derivative of dietary Vitamin A and beta-carotene).

Methods for Activating Peripheral Blood Mononuclear Cells (PBMCs)

According to one aspect, the present invention provides a method for activation of PBMCs, the method comprising the steps:

a) administering a wild-type HIV Tat protein to a cell culture, the cell culture comprising cells, wherein the cells are PBMCs;

b) maintaining the cell culture at physiological oxygen levels;

c) activating the cells of the cell culture; and d) obtaining a phenotypically converted activated PBMC population.

The term "activation" as used herein refers to a phenotypic conversion of a cell. The term "phenotype" as used herein refers to any observable characteristic of an organism, such as its morphology, development, biochemical or physiological properties, or behavior. The term "conversion" as used herein refers to the process or result of changing from one appearance, state, or phase to another and/or to becoming susceptible to HIV infection if incubated with the virus in a standard in vitro infection protocol.

According to another embodiment, the cells of step (a) are non-HIV infected cells.

According to another embodiment, the activated cells of step (c) has a memory T-cell phenotype. According to some such embodiments, the activated cells of step (c) have biomarkers selected from the group consisting of $CD45Ro^{(+)}$, $CD95^{(+)}$, $CD62L^{(+)}$ and $CD45RA^{(-)}$. According to some such embodiments, the activated cells of step (c) have a CD3 dull phenotype by flow cytometry.

According to another embodiment, the phenotypically converted PBMC cell population constitutes at least about 20% the cell population. According to another embodiment, the phenotypically converted PBMC cell population constitutes at least 5% of the cell population.

According to another embodiment, the converted population is washed to remove the Tat, incubated for 3 hours with HIV virus, washed to remove the virus and incubated for 6 days to allow production of virus into the culture and measurement of the produced virus.

According to another embodiment, the cell culture is cultured at an oxygen concentration physiologically appropriate for the cell. According to some such embodiments, the oxygen concentration is from about 2% oxygen to about 10% oxygen. According to some such embodiments, the oxygen concentration is about 2% oxygen. According to some such embodiments, the oxygen concentration is about 3% oxygen. According to some such embodiments, the oxygen concentration is about 4% oxygen. According to some such embodiments, the oxygen concentration is about 5% oxygen. According to some such embodiments, the oxygen concentration is about 6% oxygen. According to some such embodiments, the oxygen concentration is about 7% oxygen. According to some such embodiments, the oxygen concentration is about 8% oxygen. According to some such embodiments, the oxygen concentration is about 9% oxygen. According to some such embodiments, the oxygen concentration is about 10% oxygen. According to another embodiment, the cell culture is cultured at oxygen levels that approximate those encountered by lymphocytes in vivo. According to some such embodiments, the cell culture is maintained at about 5% oxygen. According to some such embodiments, the cell culture is maintained at about 5% carbon dioxide. According to some such embodiments, the cell culture is maintained at about 37° C.

According to another embodiment, the wild-type HIV TAT protein is of an amount sufficient for activation of PBMCs. According to some such embodiments, Tat protein is provided in amounts from about 1 ng/ml to about 100 μg/ml. According to some such embodiments, Tat protein is provided in amounts of about 5 μg/ml. According to another embodiment, the Tat protein is substantially similar to wild-type HIV Tat protein.

According to another embodiment, the wild-type HIV Tat protein has a polypeptide sequence of substantial similarity to the polypeptide sequence [SEQ ID NO: 1], wherein the wild-type HIV Tat protein further comprises a conserved segment, wherein the conserved segment is of the formula:

X1-X2-X3-X4-X5-X6-X7-X8-X9-X10-X11-X12-X13-X14-X15-X16-X17-X18-X19-X20 [SEQ ID NO: 12]

wherein X1 is A; X2 is C; X3 is T; X4 is N; X5 is C; X6 is Y;.X7 is C; X8 is K; X9 is K; X10 is C; X11 is C; X12 is F; X13 is H; X14 is C; X15 is Q; X16 is V; X17 is C; X18 is F; X19is I; and X20 is T.

According to another embodiment, the wild-type HIV Tat protein is a recombinant protein. As used herein, the term "recombinant" refers to of or resulting from new combinations of genetic material. According to another embodiment, the Tat protein is a Tat protein substantially similar to the wild-type HIV Tat protein.

According to another embodiment, the present invention provides a Tat protein substituted for PHA/IL-2 for use as a mitogen for priming (meaning increasing sensitivity to) and support of HIV infection.

Methods for Identification of Blocking Agents of Tat Protein Activity

According to another aspect, the present invention provides methods useful for the identification of blocking agents of Tat protein activation of peripheral blood mononuclear cells (PBMCs).

According to one embodiment, the present invention provides a method useful for the identification of blocking agents of Tat protein activation of peripheral blood mononuclear cells (PBMCs), the method comprising the steps:

a) providing a cell culture, the cell culture comprising cells, wherein the cells are PBMCs;
b) administering a Tat protein to the cell culture;
c) administering a blocking agent to the cell culture;
d) maintaining the cell culture at physiological oxygen levels;

wherein the blocking agent associates with the Tat protein, wherein the blocking agent associates with an active portion of the Tat protein, thereby preventing a phenotypic conversion of the PBMC cell population.

According to another embodiment, the cell culture is cultured at oxygen levels that approximate those encountered by lymphocytes in vivo. According to some such embodiments, the cell culture is maintained at about 5% oxygen. According to some such embodiments, the cell culture is maintained at about 5% carbon dioxide. According to another embodiment, the cell culture is cultured at an oxygen concentration physiologically appropriate for the cell. According to some such embodiments, the oxygen concentration is from about 2% oxygen to about 10% oxygen. According to some such embodiments, the oxygen concentration is about 2% oxygen. According to some such embodiments, the oxygen concentration is about 3% oxygen. According to some such embodiments, the oxygen concentration is about 4% oxygen. According to some such embodiments, the oxygen concentration is about 5% oxygen. According to some such embodiments, the oxygen concentration is about 6% oxygen. According to some such embodiments, the oxygen concentration is about 7% oxygen. According to some such embodiments, the oxygen concentration is about 8% oxygen. According to some such embodiments, the oxygen concentration is about 9% oxygen. According to some such embodiments, the oxygen concentration is about 10% oxygen.

According to another embodiment, the wild-type HIV Tat protein is of an amount sufficient for activation of PBMCs. According to some such embodiments, Tat protein is provided in amounts from about 1 ng/ml to about 100 μg/ml. According to some such embodiments, Tat protein is provided in amounts of about 5 μg/ml. According to another embodiment, the Tat protein is substantially similar to wild-type HIV Tat protein.

According to another embodiment, the Tat protein is a wild-type HIV Tat protein. According to some such embodiments, the wild-type HIV Tat protein has a polypeptide sequence of substantial similarity to the polypeptide sequence [SEQ ID NO: 1], wherein the wild-type HIV Tat protein further comprises a conserved segment, wherein the conserved segment is of the formula:

X1-X2-X3-X4-X5-X6-X7-X8-X9-X10-X11-X12-X13-X14-X15-X16-X17-X18-X19-X20 [SEQ ID NO: 12]

wherein X1 is A; X2 is C; X3 is T; X4 is N; X5 is C; X6 is Y; X7 is C; X8 is K; X9 is K; X10 is C; X11 is C; X12 is F; X13 is H; X14 is C; X15 is Q; X16 is V; X17 is C; X18 is F; X19 is I; and X20 is T.

The term "active portion" as used herein refers to the part of the Tat protein that enables TAT protein activation of PBMCs.

The term "associate" or "associates" as used herein refers to joining, connecting, or combining to, either directly, indirectly, actively, inactively, inertly, non-inertly, completely or incompletely.

The term "antagonist" as used herein refers to a substance that counteracts the effects of another substance. The term "agonist" as used herein refers to a chemical substance capable of activating a receptor to induce a full or partial pharmacological response. The term "blocker" or "blocking agent" as used herein refers to a substance that inhibits the physiological action of another substance. The term "inhibitor" as used herein refers to an agent that interferes with or prevents the activity of a protein, molecule, nucleic acid, or other substance.

According to some such embodiments, the active portion is the conserved segment.

According to some embodiments, the blocking agent is an inhibitor.

According some embodiments, the blocking agent is an antagonist.

According some embodiments, the blocking agent is an antibody.

As used herein, the term "antibody" includes, by way of example, both naturally occurring and non-naturally occurring antibodies. Specifically, the term "antibody" includes polyclonal antibodies and monoclonal antibodies, and fragments thereof. Furthermore, the term "antibody" includes chimeric antibodies and wholly synthetic antibodies, and fragments thereof. The terms "epitope" and "antigenic determinant" are used interchangeably herein to refer to the site on a molecule that an antibody combining site (ACS) recognizes and to which that antibody binds/attaches itself. An epitope may be an antigenic determinant/antigen binding site on Tat. The epitope may be primary, secondary, or tertiary-sequence related.

According to another embodiment, the blocking agent is an antibody or antibody fragment that specifically binds to at least a segment of a polypeptide substantially similar to [SEQ ID NO: 1]. According to another embodiment, the blocking agent is an antibody or antibody fragment that specifically binds to at least a segment of a polypeptide substantially similar to [SEQ ID NO: 2].

Methods of Identifying an Active Portion of Tat polypeptide Useful as an Immunogen According to one aspect, the present invention provides methods useful for identifying an active portion of a Tat polypeptide for incorporation as an immunogen in vaccines.

The term "vaccine" as used herein refers to a biological preparation which is used to establish or improve immunity to a particular disease.

According to one embodiment, the present invention provides a method for identifying an active portion of a Tat polypeptide for incorporation as an immunogen in a vaccine, the method comprising the steps:

a) providing a cell culture, the cell culture comprising cells, wherein the cells are PBMCs;
b) maintaining the cell culture at physiological oxygen levels;

c) administering a Tat polypeptide to the cell culture;

d) administering a blocking agent to the cell culture;

wherein the blocking agent associates with an active portion of the Tat polypeptide such that Tat polypeptide activity is reduced;

e) isolating the segment of the Tat polypeptide that specifically associates with the blocking agent, wherein the segment comprises the active portion;

f) incorporating the active portion of step (e) into a vaccine;

whereby the vaccine provides an immunogenic response to the Tat active portion.

According to another embodiment, the Tat protein is a wild-type HIV Tat protein. According to another embodiment, the wild-type HIV Tat protein has a polypeptide sequence of substantial similarity to the polypeptide sequence [SEQ ID NO: 1].

According to another embodiment, the cell culture is cultured at oxygen levels that approximate those encountered by lymphocytes in vivo. According to some such embodiments, the cell culture is maintained at about 5% oxygen. According to some such embodiments, the cell culture is maintained at about 5% carbon dioxide. According to another embodiment, the cell culture is cultured at an oxygen concentration physiologically appropriate for the cell. According to some such embodiments, the oxygen concentration is from about 2% oxygen to about 10% oxygen. According to some such embodiments, the oxygen concentration is about 2% oxygen. According to some such embodiments, the oxygen concentration is about 3% oxygen. According to some such embodiments, the oxygen concentration is about 4% oxygen. According to some such embodiments, the oxygen concentration is about 5% oxygen. According to some such embodiments, the oxygen concentration is about 6% oxygen. According to some such embodiments, the oxygen concentration is about 7% oxygen. According to some such embodiments, the oxygen concentration is about 8% oxygen. According to some such embodiments, the oxygen concentration is about 9% oxygen. According to some such embodiments, the oxygen concentration is about 10% oxygen.

According to another embodiment, the wild-type HIV Tat protein is of an amount sufficient for activation of PBMCs. According to some such embodiments, Tat protein is provided in amounts from about 1 ng/ml to about 100 μg/ml. According to some such embodiments, Tat protein is provided in amounts of about 5 μg/ml. According to another embodiment, the Tat protein is substantially similar to wild-type HIV Tat protein [SEQ ID NO:1].

The term "specifically" as used herein refers to having a particular effect on only one substance or molecule, or affecting it in only one way.

According to another embodiment, the vaccine further comprises an adjuvant.

The term "adjuvant" is used herein to refer to an agent which, while not having any specific antigenic effect in itself, may stimulate the immune system to increase the response to a vaccine. An adjuvant contributes to achieving a potent immune response in various ways. First, it acts as a depot or reservoir, whereby the antigen is released progressively (e.g., mineral or oil compounds). In this way the macrophages phagocytose antigen for a longer period of time. Second, the adjuvant is able to present the antigen directly to the competent cells (macrophages, dendritic cells of the lymph nodes, etc.). As used herein, the term "competent cell" refers to a cell having ability to take up extracellular DNA from its environment. For example, liposomes and microspheres avoid metabolization and elimination of the antigen contained within them-thus ensuring that the contained antigen is fundamentally presented to macrophages, which in turn transport the antigen to the lymph nodes where the immune response takes place. Third, some adjuvants act as chemical immune stimulators of lymphoid cells (lipopolysaccharides, cytokines, lipid A, Freund, etc.). Of course, some vaccine formulations may combine several of these mechanisms. For example, an immune enhancer such as lipid A may be incorporated into the liposomes, followed by inoculation with aluminum hydroxide to thus create a reservoir. Fourth, some adjuvants may stimulate immune cells to produce cytokines, which then may act on a variety of immune cells to produce stronger humoral or cellular responses.

The most commonly used adjuvants are aluminum (alum) based compounds such as, for example, aluminum hydroxide. Aluminum hydroxide adjuvant has been used in billions of doses of vaccines for other diseases and is effective at increasing the length of time an antigen is present, from days to as much as weeks. Recent studies on aluminum hydroxide adjuvant show that it stimulates the production of specific types of immune cells called antigen presenting cells (APCs), which pick up the antigen and present it to T cells.

Mixtures of adjuvant compounds are becoming increasingly popular. Among these is a mixture of MPL (monophosphoryl lipid A) plus alum, called AS04 (GlaxoSmithKline). AS02 (GlaxoSmithKline) is an adjuvant that contains an oil-in-water mix and MPL plus saponin, a plant extract.

Immunogens

The terms "immunogen" or "antigen" are used interchangeably herein and refer to a substance that prompts the generation of antibodies and that can provoke an immune response.

According to one aspect, the present invention provides an immunogen comprising an isolated variant of wild-type HIV Tat protein, wherein the isolated variant has a polypeptide sequence of substantial similarity to [SEQ ID NO: 1], wherein the isolated variant further comprises a conserved segment, wherein the conserved segment is of the formula:

X1-X2-X3-X4-X5-X6-X7-X8-X9-X10-X11-X12-X13-X14-X15-X16-X17-X18-X19-X20 [SEQ ID NO: 11] [Formula 1]

wherein X1 is A; X2 is C or S; X3 is T; X4 is N; X5 is C or S; X6 is Y; X7 is C or S; X8is K; X9 is K; X10 is C or S; X11 is C or S; X12 is F; X13 is H; X14 is C or S; X15 is Q; X16 is V; X17 is C or S; X18 is F; X19 is I; X20 is T; wherein at least one of X2, X5, X7, X10, X11, X14 and X17 is S; and wherein the isolated variant exhibits reduced HIV priming of competent cells in comparison to the wild-type HIV Tat protein.

According to one embodiment, the immunogen further comprises an adjuvant.

According to another embodiment, the Tat protein is a protein substantially similar to wild-type HIV Tat protein.

According to another aspect, the present invention provides an immunogen comprising an isolated variant of wild-type HIV Tat protein, wherein the isolated variant exhibits reduce HIV priming of competent cells in comparison to wild-type HIV Tat protein.

According to one embodiment, the wild-type HIV Tat protein is a protein having the polypeptide sequence MEPVDPRLEP WKHPGSQPKT ACTNCYCKKC CFHCQVCFIT KALGISYGRK KRRQRRRAHQ NSQTHQASLS KQPTSQPRGD PTGPKEXKKK VERETETDPF [SEQ ID NO: 1].

According to another embodiment, the immunogen comprises an isolated variant of wild-type HIV Tat protein, wherein the isolated variant comprises at least one serine for cysteine substitution at a position selected from the group consisting of position 22, position 25, position 27, position 30, position 31, position 34 and position 37 on the wild-type HIV Tat protein.

According to another embodiment, the immunogen comprises an isolated variant of wild-type HIV Tat protein having a serine for cysteine substitution at position 22 of the wild-type HIV Tat protein, wherein the isolated variant exhibits reduced HIV priming of competent cells in comparison to wild-type HIV Tat protein. In some such embodiments, the immunogen is of the polypeptide sequence MEPVDPRLEP WKHPGSQPKT ASTNCYCKKC CFHCQVCFIT KALGISYGRK KRRQRRRAHQ NSQTHQASLS KQPTSQPRGD PTGPKEXKKK VERETETDPF [SEQ ID NO: 4].

According to another embodiment, the immunogen comprises an isolated variant of wild-type HIV Tat protein having a serine for cysteine substitution at position 25 of the wild-type HIV Tat protein, wherein the isolated variant exhibits reduced HIV priming of competent cells in comparison to wild-type HIV Tat protein. In some such embodiments, the immunogen is of the polypeptide sequence MEPVDPRLEP WKHPGSQPKT ACTNSYCKKC CFHCQVCFIT KALGISYGRK KRRQRRRAHQ NSQTHQASLS KQPTSQPRGD PTGPKEXKKK VERETETDPF [SEQ ID NO: 5].

According to another embodiment, the immunogen comprises an isolated variant of wild-type HIV Tat protein having a serine for cysteine substitution at position 27 of the wild-type HIV Tat protein, wherein the isolated variant exhibits reduced HIV priming of competent cells in comparison to wild-type HIV Tat protein. In some such embodiments, the immunogen is of the polypeptide sequence MEPVDPRLEP WKHPGSQPKT ACTNCYSKKC CFHCQVCFIT KALGISYGRK KRRQRRRAHQ NSQTHQASLS KQPTSQPRGD PTGPKEXKKK VERETETDPF [SEQ ID NO: 6].

According to another embodiment, the immunogen comprises an isolated variant of wild-type HIV Tat protein having a serine for cysteine substitution at position 30 of the wild-type HIV Tat protein, wherein the isolated variant exhibits reduced HIV priming of competent cells in comparison to wild-type HIV Tat protein. In some such embodiments, the immunogen is of the polypeptide sequence MEPVDPRLEP WKHPGSQPKT ACTNCYCKKS CFHCQVCFIT KALGISYGRK KRRQRRRAHQ NSQTHQASLS KQPTSQPRGD PTGPKEXKKK VERETETDPF [SEQ ID NO: 7].

According to another embodiment, the immunogen comprises an isolated variant of wild-type HIV Tat protein having a serine for cysteine substitution at position 31 of the wild-type HIV Tat protein, wherein the isolated variant exhibits reduced HIV priming of competent cells in comparison to wild-type HIV Tat protein. In some such embodiments, the immunogen is of the polypeptide sequence MEPVDPRLEP WKHPGSQPKT ACTNCYCKKC SFHCQVCFIT KALGISYGRK KRRQRRRAHQ NSQTHQASLS KQPTSQPRGD PTGPKEXKKK VERETETDPF [SEQ ID NO: 8].

According to another embodiment, the immunogen comprises an isolated variant of wild-type HIV Tat protein having a serine for cysteine substitution at position 34 of the wild-type HIV Tat protein, wherein the isolated variant exhibits reduced HIV priming of competent cells in comparison to wild-type HIV. In some such embodiments, the immunogen is of the polypeptide sequence MEPVDPRLEP WKHPGSQPKT ACTNCYCKKC CFHSQVCFIT KALGISYGRK KRRQRRRAHQ NSQTHQASLS KQPTSQPRGD PTGPKEXKKK VERETETDPF [SEQ ID NO: 9].

According to another embodiment, the immunogen comprises an isolated variant of wild-type HIV Tat protein having a serine for cysteine substitution at position 37 of the wild-type HIV Tat protein, wherein the isolated variant exhibits reduced HIV priming of competent cells in comparison to wild-type HIV Tat protein. In some such embodiments, the immunogen is of the polypeptide sequence MEPVDPRLEP WKHPGSQPKT ACTNCYCKKC CFHSQVCFIT KALGISYGRK KRRQRRRAHQ NSQTHQASLS KQPTSQPRGD PTGPKEXKKK VERETETDPF [SEQ ID NO: 10].

Diagnostic Kit

According to one aspect, the present invention provides a diagnostic kit for identifying blocking agents for HIV Tat protein, the kit comprising components:

a) a cell population comprising cells, wherein the cells are peripheral mononuclear blood cells; wherein the cell population is to be maintained in a $CO_2$ incubator at an oxygen concentration physiologically appropriate for the cell;

b) a stimulating agent having a polypeptide sequence substantially similar to [SEQ ID NO:1];

c) a putative blocking agent;

d) a means for admixing component (a), component (b), and component (c);

wherein the blocking agent associates with the stimulating agent of component (b), thereby preventing stimulating agent activation of the cell population of component (a).

According to one embodiment, the stimulating agent is Tat.

According to another embodiment, the oxygen concentration is from about 2% oxygen to about 10% oxygen. According to some such embodiments, the oxygen concentration is about 2% oxygen. According to some such embodiments, the oxygen concentration is about 3% oxygen. According to some such embodiments, the oxygen concentration is about 4% oxygen. According to some such embodiments, the oxygen concentration is about 5% oxygen. According to some such embodiments, the oxygen concentration is about 6% oxygen. According to some such embodiments, the oxygen concentration is about 7% oxygen. According to some such embodiments, the oxygen concentration is about 8% oxygen. According to some such embodiments, the oxygen concentration is about 9% oxygen. According to some such embodiments, the oxygen concentration is about 10% oxygen.

According to another embodiment, the stimulating agent is of an amount sufficient for activation of peripheral blood mononuclear cells.

According to another embodiment, the stimulating agent is provided in amounts from about 1 ng/ml to about 100 µg/ml.

According to another embodiment, the blocking agent is an inhibitor.

According to another embodiment, the blocking agent is an antagonist.

According to another embodiment, the blocking agent is an agonist. According to another embodiment, the kit further provides component (e): a means of analyzing the cells within component (d). According to some such embodiments, the means of analyzing the cells of component (d) is flow cytometry.

The term "admixing" is used herein to refer to mingle with, to add to something else, to mix, to put together into one mass so that the constituent parts are more or less homogeneous, to amalgamate, to blend, to comingle, to commix, to fuse, to intermingle, to intermix, to merge, or to stir. Admixing may occur in any appropriate vessel, container, bag, barrel, bin, bottle, bucket, cage, can, canister, canteen, capsule, case, cask, cup, decanter, drum, flask, holder, jug, keg, magnum, pail, pod, pot, pouch, receptacle, shaker, tank, tin, tub, vat, or vial by shaking, pipetting, rotating, vibrating, twirling, swirling, bubbling, inverting, or tossing.

Unless defined otherwise, all technical and scientific terms used herein have the same meaning as commonly understood by one of ordinary skill in the art to which this invention belongs. Any methods and materials similar or equivalent to those described herein can also be used in the practice or testing of the present invention.

It must be noted that as used herein and in the appended claims, the singular forms, "a, and", and "the" include plural references unless the context clearly dictates otherwise. All technical and scientific terms used herein have the same meaning. Efforts have been made to ensure accuracy with respect to numbers used (e.g. amounts, temperature, etc.) but some experimental errors and deviations should be accounted for.

Where a range of values is provided, it is understood that each intervening value, to the tenth of the unit of the lower limit, unless the context clearly dictates otherwise, between the upper and lower limit of the range and any other stated or intervening value in that stated range, is encompassed within the invention. The upper and lower limits of these small ranges which may independently be included in the smaller rangers is also encompassed within the invention, subject to any specifically excluded limit in the stated range. Where the stated range includes one or both of the limits, ranges excluding either or both of those included limits are also included in the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. It is intended that the scope of the invention be construed to include all modifications and alterations that may occur to others upon reading and understanding the preceding detailed description insofar as they come within the scope of the following claims or equivalents thereof. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methodologies

Cell stimulation and short-term culture were carried out at two levels of oxygen. A five percent oxygen tension incubator was generated in a Sanyo MCO-175M $O_2/CO_2$ incubator (Sanyo Scientific, Bensenville, Ill.). In this incubator, gas-phase oxygen tension is controlled by continuous injection of appropriate amounts of medical grade nitrogen ($N_2$) in order to reach 5% oxygen (physiologic oxygen levels, "physO2"). Cells cultured at atmospheric oxygen levels (20% oxygen, "atmosO$_2$") were incubated in a standard incubator without additional supply of nitrogen. $CO_2$ levels were maintained at 5% in both cases.

PBMCs from healthy individuals were obtained from blood drawn after informed consent and immediately before initiation of the experiment. The blood was drawn into tubes containing heparin (Vacutainer, Becton Dickinson). PBMC was isolated by gradient centrifugation on Ficoll-Hypaque (Amersham Pharmacia).

Recombinant HIV-1 transactivator of transcription (Tat) protein as well as a Cysteine to Serine variant of wild type Tat was obtained. This preparation was endotoxin free, meaning that the levels of endotoxin in the preparation had been measured and shown to be negligible.

Wild type and variant Tat proteins were conjugated to the AlexaFluor-488 carboxylic-acid, succinimidyl ester (Molecular Probes, Invitrogen, Carlsbad, Calif.), according to the manufacturers protocol for conjugation of proteins with slight modification to suit the low molecular weight protein. The conjugated Tat was separated from unconjugated dye by standard methods. AlexaFluor conjugated Tat protein was used to detect entry of the polypeptide into isolated PBMCs in culture.

Supernatants from cultured cells were isolated and centrifuged. Cell free supernatant aliquots then were frozen at −80° C. for p24 ELISA determinations. p24 is a protein that surrounds the viral RNA within the envelope of HIV and is a marker of HIV infection. p24 levels in the culture supernatant were determined using a Beckman Coulter kit for quantitative measurement of HIV-1 p24 antigen (EIA-assay) according to the instructions provided by the manufacturer. Briefly, aliquots of the conditioned culture media, positive (purified p24 antigen) controls, and negative controls provided by the manufacturer were diluted. The samples then were applied to the pre-coated antibody plate. The plate was sealed and incubated for 60 minutes at 37° C. Unbound antigen was removed by washing and bound antigen then detected using a biotin labeled antibody, Streptavidin, and substrate. Absorbance was measured at 450 nm in a Labsystem Multiskan RC (Fisher Scientifics).

High Dimensional Fluorescence Activated Cell Sorter (Hi-D FACS) Analysis was performed. Antibodies against cell surface markers were used to distinguish T cells, B cells, T memory cells and naive subsets. The antibodies were obtained from BD-PharMingen (San Diego, Calif.) and were later conjugated according to the protocols available at http://www.drmr.com/abcon/index.html (last visited Aug. 17, 2007). Briefly, fluorophores (10 mg) were dissolved in 1 mL anhydrous DMSO. Each fluorophore was added to give a ratio of 40-80 µg fluorophore per mg of antibody and mixed immediately. The solution was wrapped in foil, incubated and rotated at 25° C. for 1 hour. The unreacted fluorophore then was removed, and the antibody exchanged into a storage buffer (10 mM Tris, 150 mM NaCl, 0.1% $NaN_3$, pH 8.2). The list of the antibodies is as follows; CD3, CD4, CD8, CD45RA, CD45RO, CD62L and CD11a. Briefly, cells were washed in media containing probenecid (Sigma, St. Louis, Mo.) and fetal calf serum, pH 7.4, then stained with MCB (Mono-Chlorobimane, Molecular probes, Invitrogen) for 20 minutes at room temperature, before staining with a cocktail of fluorophore conjugated antibodies against cell subtype markers for 15 minutes. Cells then were resuspended in staining media with 0.4% formaldehyde before being analyzed on the Stanford Shared FACS Facility Hi-D FACS instrument. "Flasher-II" Hi-D FACS device is a hybrid instrument in which a FACS II bench is coupled to FACS DiVa electronics. Data were analyzed with FLOWJO software (http://treestar.com).

Human PBMCs were stained with (CarboxyFluorescein DiAcetate Succinimidyl-Ester, CFDA-SE) according to Mannering et al. (*J. Immunol. Methods.* 2003 December; 283(1-2):173-83) with some modifications. Briefly, Ficoll gradient separated PBMCs were suspended at $10^6$ cells per ml in serum free RPMI medium 1640 and stained with 0.5 µM CFDA-SE for 10 min at 37° C. The reaction was terminated by addition of a 3-fold excess volume RPMI medium 1640 with 10% FCS. After 2 washes, the cells were resuspended at $10^6$ cells per ml in RPMI 1640 with 10% FCS.

The numbers of cells in the cultures were determined by FACS using BD Trucount beads according to the instructions provided by manufacturer. Briefly, 100 µl of the cell culture suspension was added to the Trucount beads. A live dead marker was also added. This mixture of cells and beads was then acquired for 250,000 events. Since the total number of beads are known in the tubes, the number of cells in 100 µl of culture is calculated. Cell viability was determined either by monochlorobimane (MCB) stain or Invitrogen Live/dead marker. Briefly, PBMCs are isolated from whole blood, incubated with MCB, then quenched. Samples then are incubated with antibodies and compensation stains (FITC, PE, CyC), mixed with deficient RPMI ((without biotin, riboflavin, phenol red, glutamine or $NaHCO_3$) with added HEPES at pH 7), then analyzed.

PBMCs were isolated from blood immediately after the blood was drawn and treated with interleukin-2 (IL-2) a cytokine that stimulates the growth of specific types of white blood cells, and phytohemagglutinin ("PHA") (50 U/ml IL-2 and 2.5 µg/ml PHA) or Tat (5 µg/ml) protein for 72 hours in RPMI 1640 media equilibrated in the given oxygen levels. Cells were exposed to 1000° C.-50 of the virus (Lai-1) for 3 hours before cells were washed and incubated in the media consisting of RPMI 20% FCS as well as either IL-2 or Tat. The cells were allowed to recover and proliferate for 3, 6, 10 days for kinetic analyses.

Analysis of FACS data, including calculations of absolute cell numbers, cell division and cell proliferation indices, were performed using the FLOWJO software (Treestar.com). Statistical analyses were performed with the JMP statistical software package (SAS institute, Cary, N.C.).

Example 1

Tat Induction of Apoptosis in PBMCs at Atmospheric Levels

PBMCs ($10^6$/ml) cultured with Tat or with PHA/IL-2 at atmospheric oxygen levels or physiological oxygen levels are seen in FIG. 1. Cells were cultured in RPMI supplemented with 5% FCS. Atmospheric oxygen ($atmosO_2$) incubators were maintained at 5% $CO_2$ equilibrated with air, resulting in an internal oxygen level of approximately 20% $O_2$. Physiologic oxygen (physO2) incubators were maintained at 5% $CO_2$ equilibrated with air and nitrogen mixed to maintain and internal oxygen level of 5% $O_2$. Tat (5 µg/ml) or PHA/IL-2 (PHA: 2.5 µg/ml; IL-2: 50 Units/ml), respectively) were added at the start of the culture period. Cells were harvested after 3 days.

The results show that Tat induction of apoptosis is extensive in PBMCs cultured at atmospheric oxygen levels (20% $O_2$) but is minimal at physiological oxygen levels (5% $O_2$). In the absence of any stimulation (media only culture), 60-70% of the cells put into culture were recovered as viable cells at the end of the culture period regardless of whether the cells were maintained at $atmosO_2$ or $physO_2$.

Example 2

Tat Induces Proliferation of PBMC Cultured at Physiological Oxygen Levels ($physO_2$)

Figure 2A:
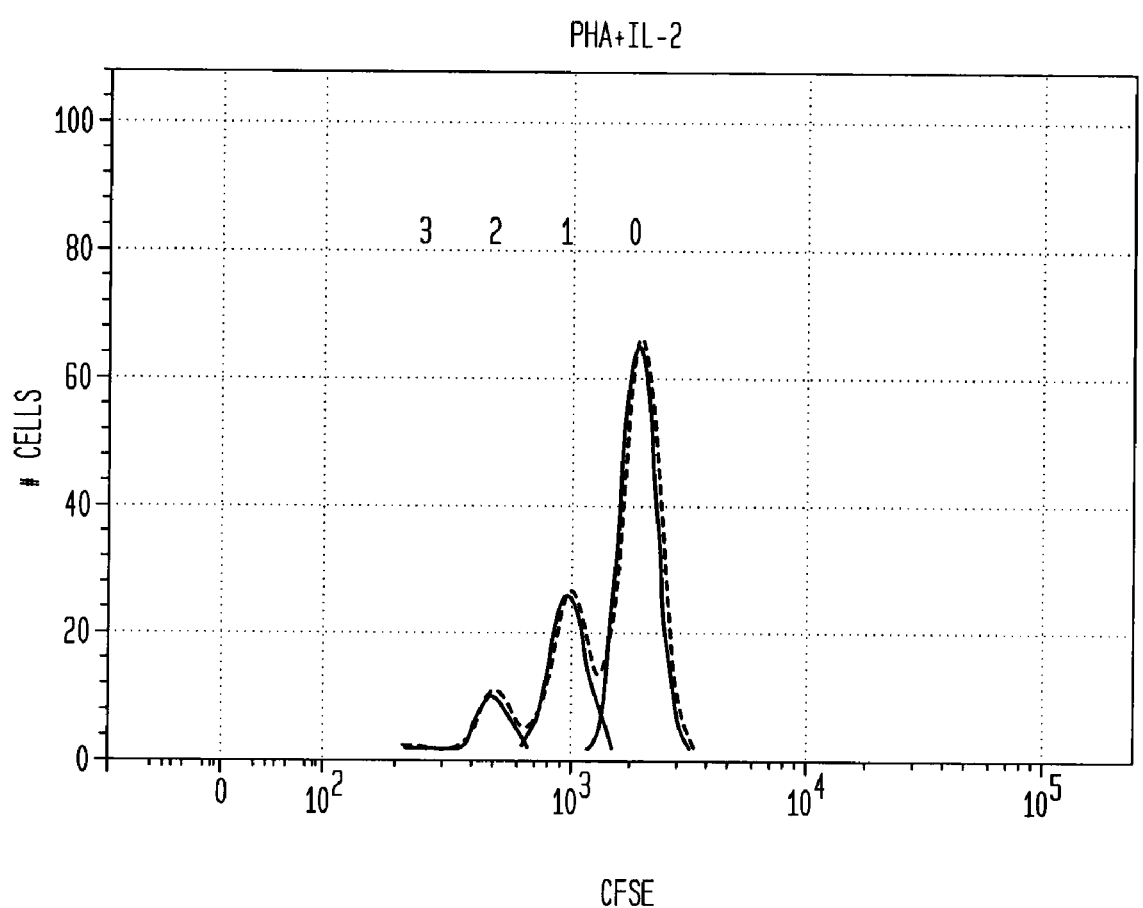

PBMCs were labeled with 0.5 µM CarboxyFluorescein DiAcetate Succinimidyl-Ester, (CFDA-SE) and incubated for 10 minutes at 37° C. Cells then were cultured for 6 days with either Tat (FIG. 2B) or IL-2/PHA (FIG. 2A) as indicated to evaluate cell division during the culture period. FACS data for CFSE staining are shown for live cells in FIGS. 2A and 2B (annexinV-negative cells with intact membrane capable of retaining glutathione); dashed curves show the computed frequencies of cells that have undergone the indicated number of cell divisions. Each division that a CFSE-stained cell underwent decreased the CFSE signal by half. The results show that at the end of the culture period, the distribution of CFSE-stained cells showed several peaks, with each peak being representative of the frequency of cells that had undergone the same number of divisions. The peak with the highest CFSE-staining reflects the frequency of cells that have not divided, and the peaks in decreasing fluorescence order represent cells that have undergone 1, 2 or 3 cell divisions.

Example 3

Entry of Fluorochrome-coupled Tat into PBMCs

Figure 3A:
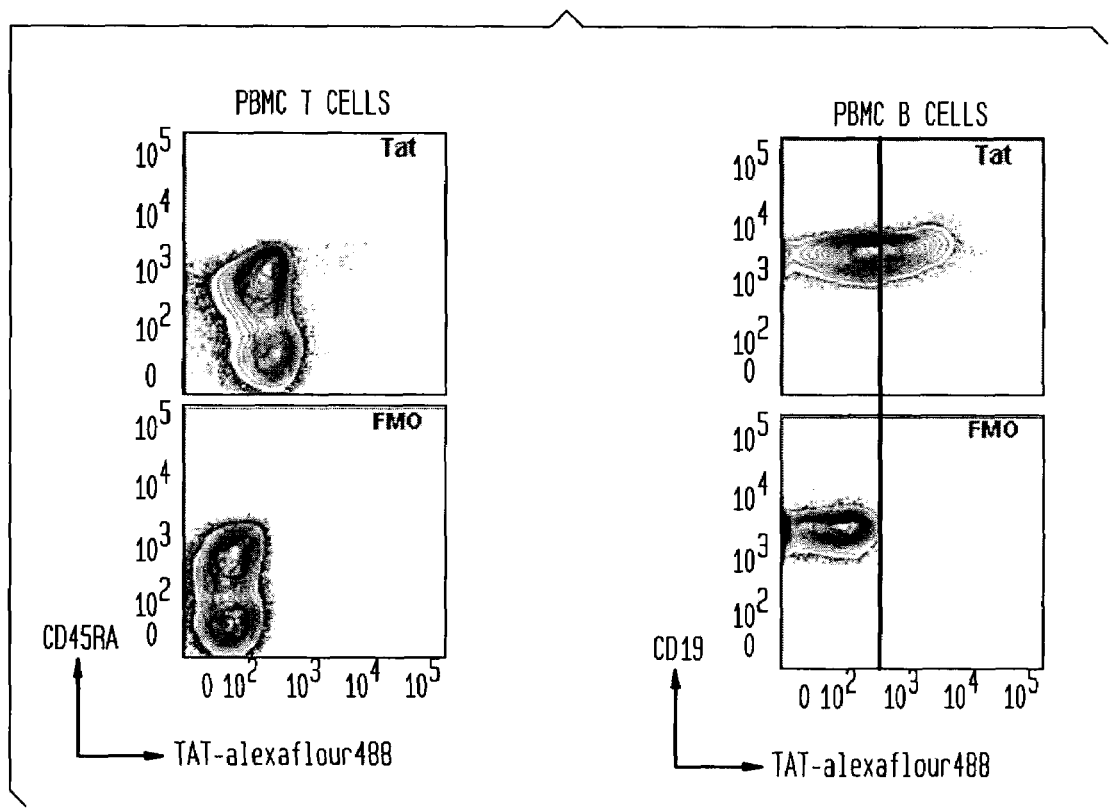
Figure 3B:
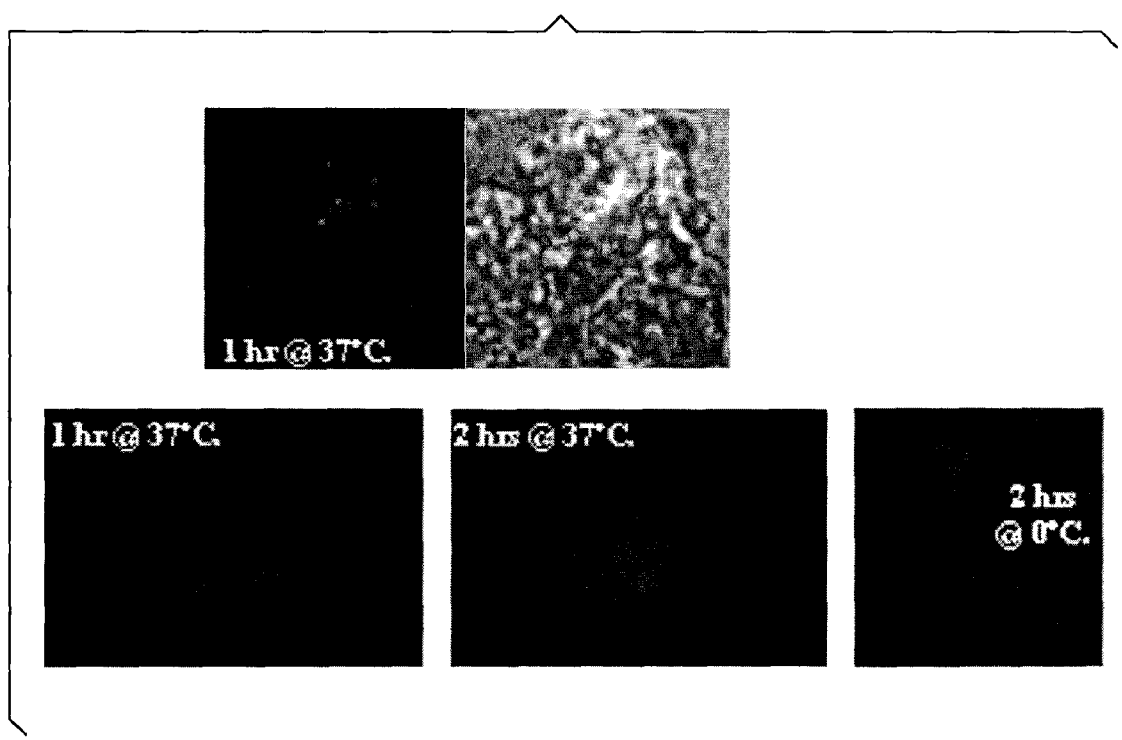

PBMCs mixed with Tat labeled with AlexaFluor488 were incubated for 2 hours at 37° C. at $physO_2$ for the indicated time periods as seen in FIGS. 3A and 3B or kept on ice. The presence of Tat in the cells was monitored by FACS and by confocal microscope. For FACS studies (FIG. 3A), cells were stained at 4° C. after incubation with Tat. Viable lymphocytes were further gated to reveal fluorescence detected in the Tat channel for cells that were not incubated with Tat but were stained with all other reagents (lower panels).

The results show that the amount of Tat detectable per cell increased with increasing time and with increasing Tat concentrations. The data shown in FIGS. 3A and 3B represent staining levels achievable with the current preparation of fluorochrome-coupled Tat at times and concentrations consistent with the Tat incubations in the examples that follow.

Example 4

The Effect of Tat on PBMC Priming for HIV Infection

Figure 4:
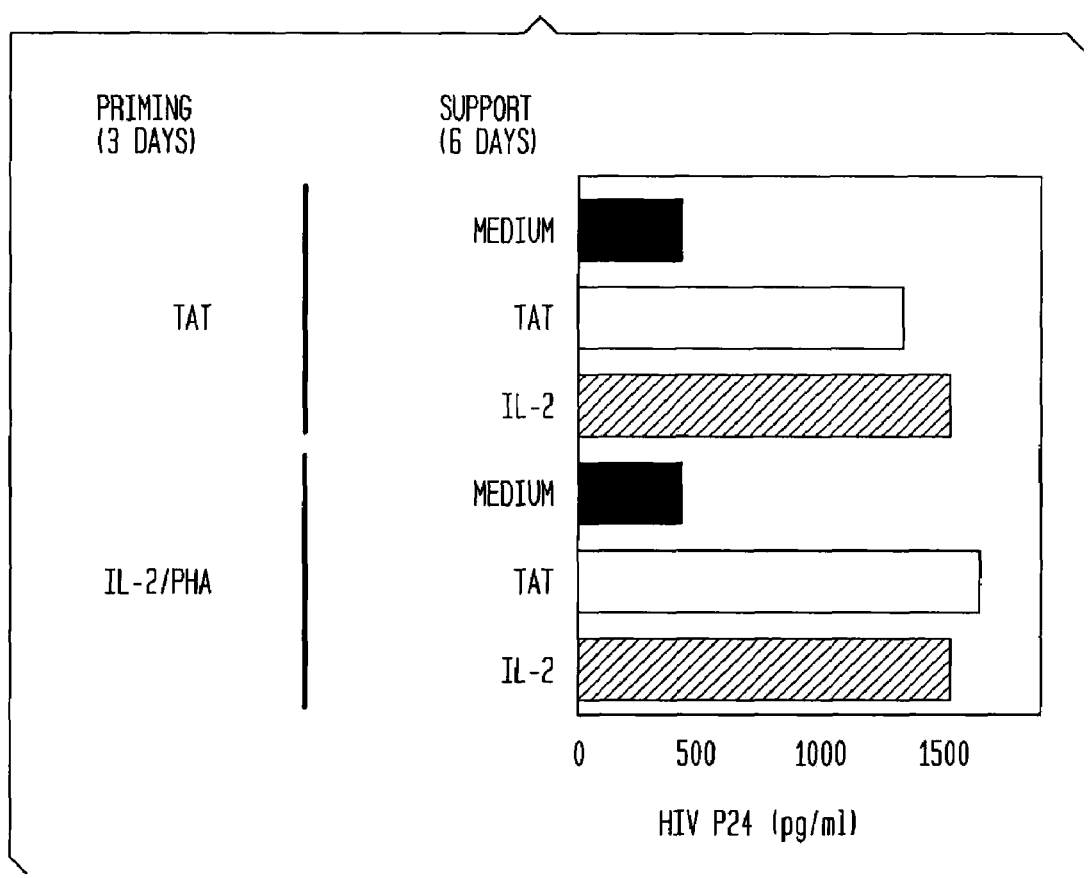

PHA/IL-2 and Tat are equivalent for this purpose. Following the standard in vitro protocol for HIV infection but maintaining the cultures at $physO_2$, PBMC were primed with PHA/IL-2 or Tat as indicated in FIG. 4 for 3 days, incubated for 3 hours with HIV (LAI) to allow infection to proceed, washed to remove free virus, and cultured for 6 days with Tat or IL-2 to allow viral production to proceed. Supernatants then were analyzed for p24 levels by ELISA.

Figure 5:
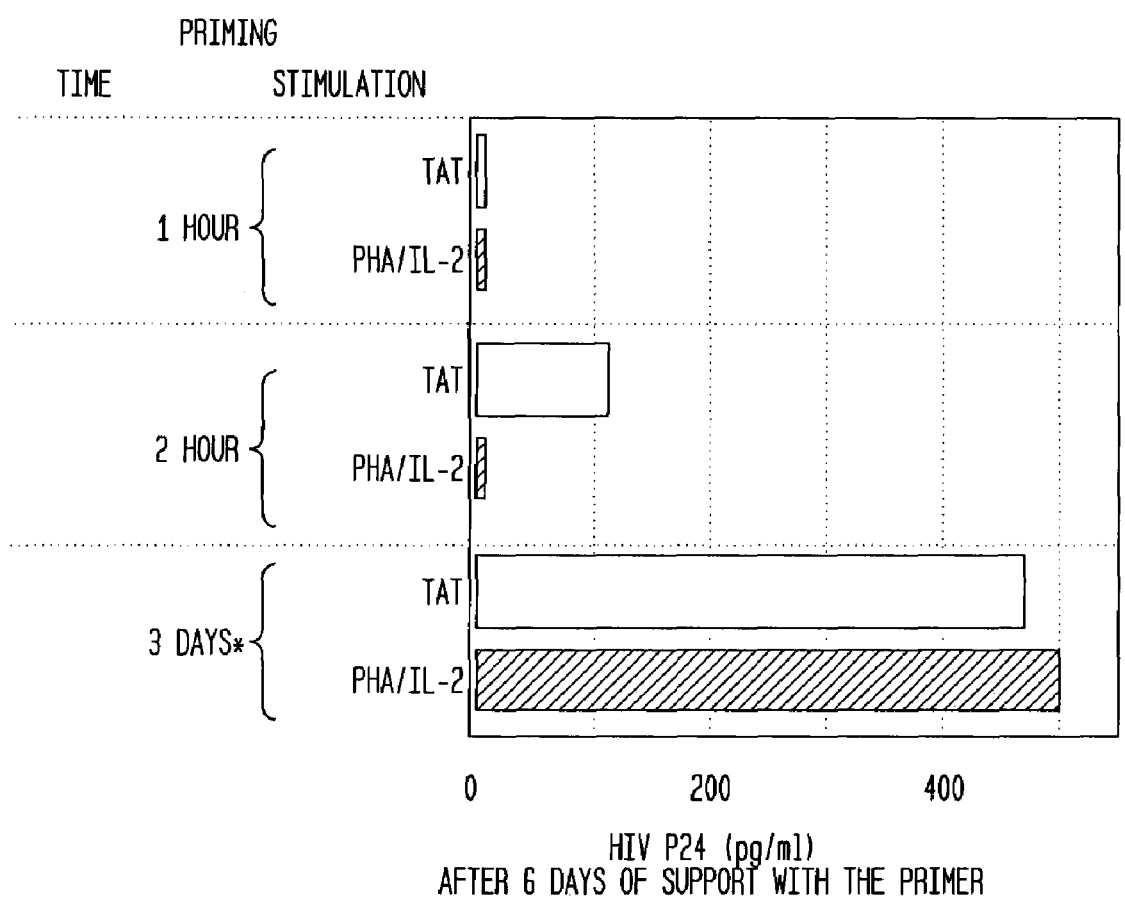

Results showed that (1) Tat primes PBMC for HIV infection in a dose dependent manner, (2) Tat is equivalent to PHA/IL-2 for priming and (3) Tat is equivalent to IL-2 for support of HIV infection. Moreover, Tat is equivalent to PHA/IL-2 stimulation in inducing cell division and fully replaces PHA/IL-2 in the standard in vitro infection protocol. As shown in FIG. 5, culturing PBMC with Tat for 2 hours is sufficient to prime for extensive HIV infection. In contrast, priming with PHA/IL-2 takes 48-72 hours.

Example 5

The Effect of Mutating Tat Cysteine Residues to Serine on Tat Priming for HIV Infection Mutating the seven Cysteine (Cys) residues to Serine (Ser) in Tat destroys priming for HIV infection. Three isolated Tat proteins were tested, including native Tat and two mutated variants of this native polypeptide. The polypeptides were tested for their ability to prime for HIV infection. IL-2 was used for the support phase in the assay.

PBMCs were primed using PHA/IL-2 with Tat, or with Tat variants Cys31 Ser or Cys22, 25, 27, 30, 31, 34, 37Ser. A p24

Figure 6:
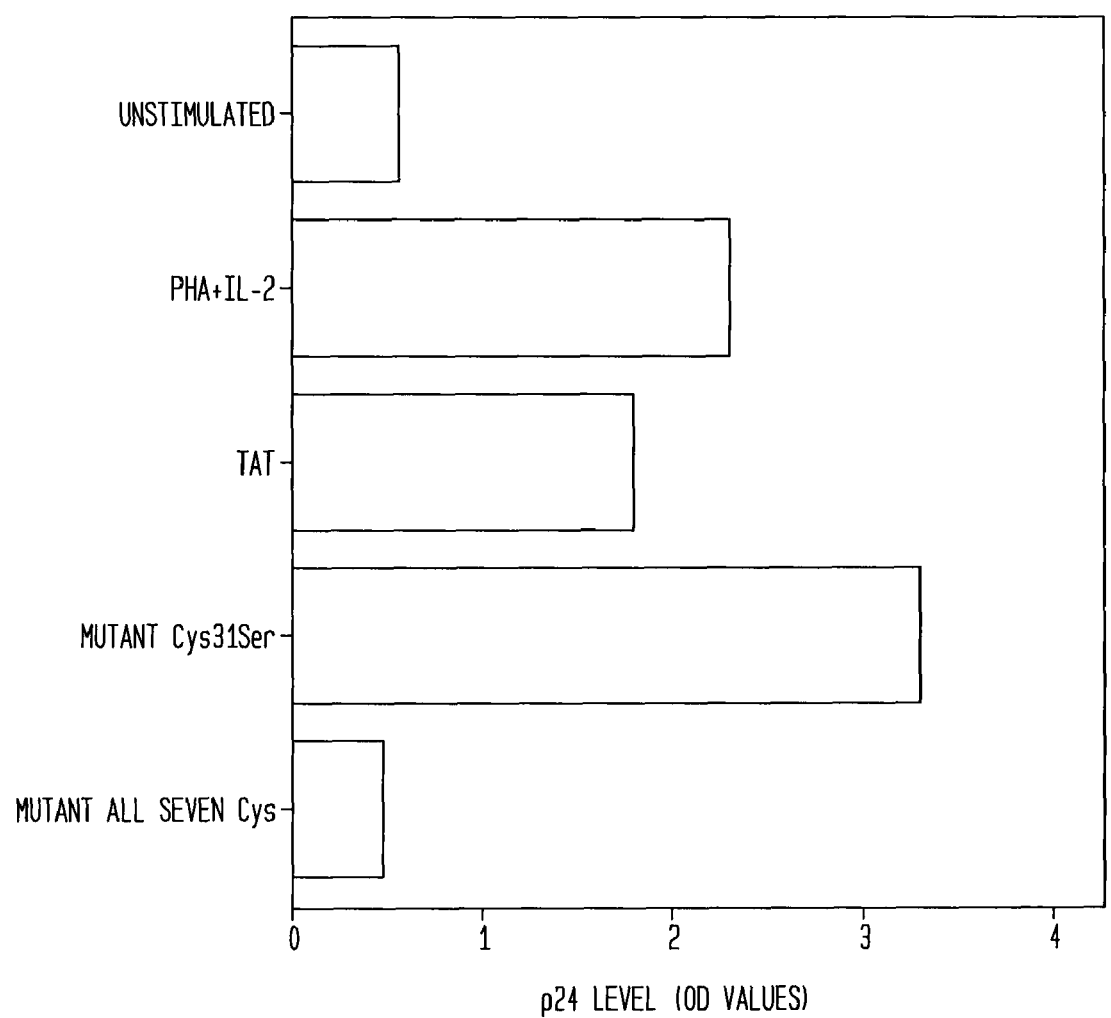

ELISA was used to determine the levels of the HIV-core protein p24 produced by infected cells after treatment with native Tat and with Tat variants Cys31 Ser, Cys22, 25, 27, 30, 31, 34, 37Ser. PBMCs were primed using PHA/IL-2. IL2 was used to support the infection. As shown in FIG. 6, the results indicate that levels for the mutated variants of Tat are low and the same as background.

Example 6

The Effect of Tat Priming on Conversion of the PBMC Phenotype

Figure 7:
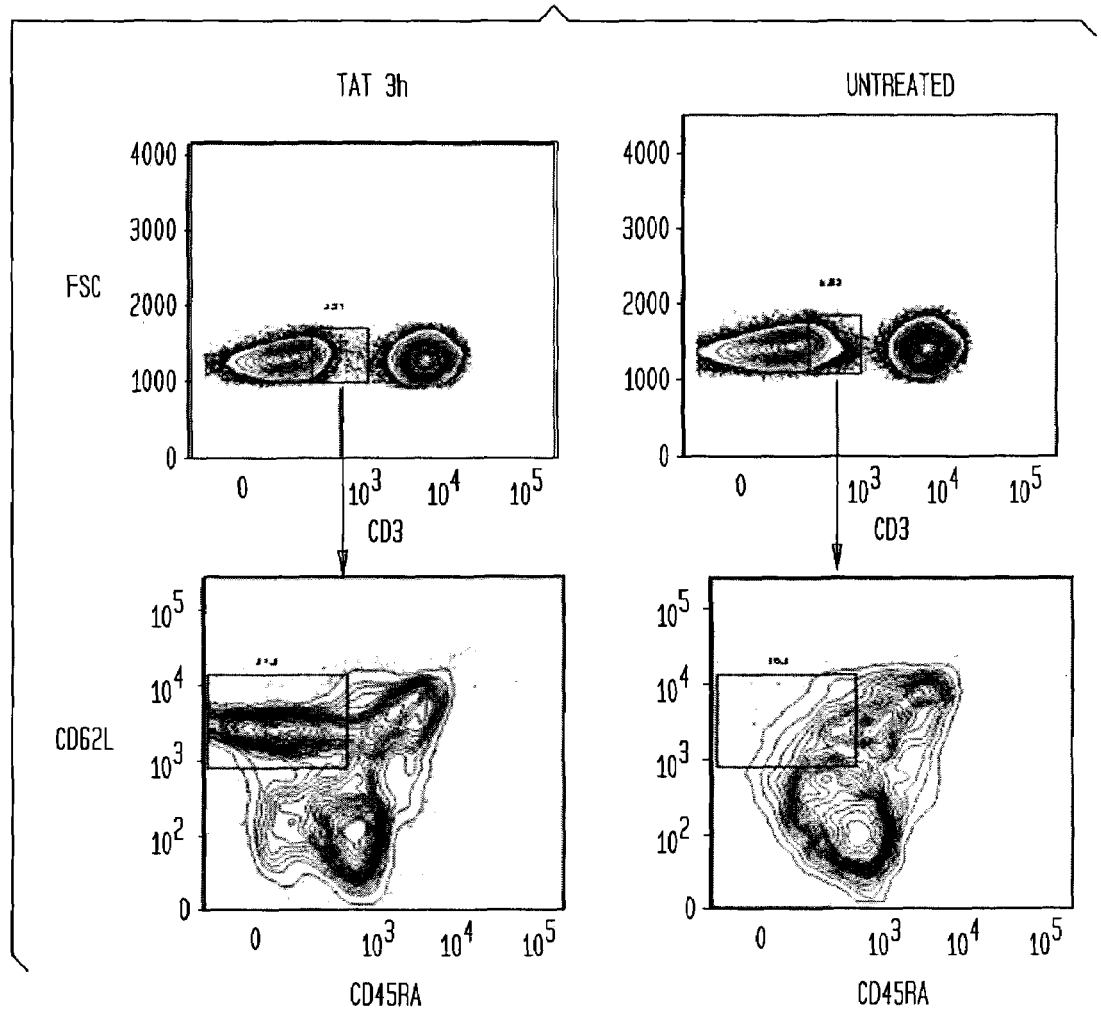

Our studies show that after 3-5 hours treatment of PBMC with Tat, a "new" subset appears that is not detectable in control PBMC cultures maintained under comparable conditions but not treated with Tat. This subset which present 3-6% of total lymphocytes most likely persists and increased in frequency to become a major T cell subset in PBMC cultures treated for 3 days. This subset is not detectable, either at 5 hours or 3 days in control cultures in which aliquots of the same PBMC preparation are cultures in the absence of Tat. Initial phenotypic determination of this new subset shows (FIG. 7) that is characterized by low level of CD3 expression, undetectable CD45RA and high levels of CD62L.

Example 7

The Effect of Mutating Tat Cysteine Residues to Serine on PBMC Phenotype Conversion The new phenotype is not detected in PBMC cultures treated with mutated Tat in which all seven cysteines are mutated to serine residues. However, this new population is detected in PBMC cultures treated with Tat with single Cys31 to serine mutation.

Example 8

Construction of Constructs Comprising Mutated Variants of Tat

The present invention envisions the preparation of constructs comprising mutated variants of Tat where the immunogenic properties of such variants are retained but the ability of such variants to enter cells and wreak havoc is removed. Since high-titer IgG secondary responses likely would be the best defense against Tat extracellular activity, such an isolated Tat variant polypeptide, or a fragment, homolog, analog or derivative thereof may be used as an immunogen in a traditional vaccination approach.

The invention has been described with reference to embodiments to illustrate the principles of the invention but not to limit the invention to the particular embodiments illustrated. Modifications and alterations may occur to others upon reading and understanding the preceding detailed description. It is intended that the scope of the invention be construed as including all modifications and alterations that may occur to others upon reading and understanding the preceding detailed description insofar as they come within the scope of the following claims or equivalents thereof.

The invention claimed is:

1. A method for phenotypically-converting immune cells in an in vitro human immunodeficiency virus (HIV) cell based activation assay, the method comprising steps:
    (a) providing a cell culture comprising competent immune cells, wherein the competent immune cells comprise a population of peripheral blood mononuclear cells, and wherein the cell culture is maintained at a physiological oxygen level; and (b) administering to the cell culture of step (a) an amount of a wild type human immunodeficiency virus (HIV)-TAT protein sufficient to convert a subset of the population of peripheral blood mononuclear cells into a phenotypically converted cell population, wherein the phenotypically converted cell population does not undergo apoptosis, and wherein the phenotypically converted cell population becomes susceptible to a human immunodeficiency virus (HIV) infection when incubated with the human immunodeficiency virus (HIV) in a standard in vitro infection.

2. The method according to claim 1, wherein the method further comprises steps for identifying an inhibitor of the wild type human immunodeficiency virus (HIV)-TAT protein, the steps comprising:

(c) administering a candidate blocking agent or a control agent to the cell culture, wherein the candidate blocking agent associates with a conserved segment of the wild type human immunodeficiency virus (HIV)-TAT protein or with the conserved segment of a variant of the wild type human immunodeficiency virus (HIV)-TAT protein, wherein the variant of the wild type human immunodeficiency virus (HIV)-TAT protein has at least 70% amino acid sequence identity to SEQ ID NO: 1.

wherein the wild type human immunodeficiency virus (HIV)-TAT protein or the variant of the wild type human immunodeficiency virus (HIV)-TAT protein comprises a conserved segment sequence of formula:

$$X1-X2-X3-X4-X5-X6-X7-X8-X9-X10-X11-X12-X13-X14-X15-X16-X17-X18-X19-X20 \quad \text{(SEQ ID NO: 11)}$$

wherein X1 is A; X2 is C or S; X3 is T; X4 is N; X5 is C or S; X6 is Y; X7 is C or S; X8 is K; X9 is K; X10 is C or S; X11 is C or S; X12 is F; X13 is H; X14 is C or S; X15 is Q; X16 is V; X17 is C or S; X18 is F; X19 is I; X20 is T, and wherein at least one of X2, X5, X7, X10, X11, X14 and X17 is S; and (d) identifying the candidate blocking agent that decreases the phenotypically converted cell population compared to the control agent as the inhibitor of the wild type human immunodeficiency virus (HIV)-TAT protein.

3. The method according to claim 1, wherein the competent immune cells in step (a) are non-HIV infected cells.

4. The method according to claim 1, wherein the phenotypically converted cell population in step (b) has a memory T-cell phenotype.

5. The method according to claim 1, wherein the phenotypically converted cell population in step (b) has at least one biomarker phenotype selected from the group consisting of $CD45Ro^{(+)}$, $CD95^{(+)}$, and $CD45RA^{(-)}$.

6. The method according to claim 1, wherein the phenotypically converted cell population in step (b) has a CD3 dull phenotype by flow cytometry.

7. The method according to claim 1, wherein the phenotypically converted cell population in step (b) constitutes at least about 20% of the population of peripheral blood mononuclear cells.

8. The method according to claim 1, wherein the cell culture in step (a) is maintained at about 5% oxygen.

9. The method according to claim 1, wherein the amount of the wild-type human immunodeficiency (HIV)-TAT protein administered in step (b) is from about 1 ng/ml to about 100 µg/ml.

10. The method according to claim 2, wherein the wild type human immunodeficiency (HIV)-TAT protein is a recombinant protein.

11. The method according to claim 2, wherein the candidate blocking agent is an antagonist.

12. The method according to claim 2, wherein the candidate blocking agent is an antibody.

13. The method according to claim 2, wherein the candidate blocking agent is an antibody fragment that specifically binds to at least a segment of the wild-type human immunodeficiency virus (HIV)-TAT protein having an amino acid sequence of at least 70% sequence identity to amino acid sequence SEQ ID NO: 1.

* * * * *

SEQUENCE LISTING

```
<160> NUMBER OF SEQ ID NOS: 12

<210> SEQ ID NO 1
<211> LENGTH: 100
<212> TYPE: PRT
<213> ORGANISM: unknown
<220> FEATURE:
<223> OTHER INFORMATION: mammalian
<220> FEATURE:
<221> NAME/KEY: MISC_FEATURE
<222> LOCATION: (87)..(87)
<223> OTHER INFORMATION: wherein the "Xaa" represents any amino acid

<400> SEQUENCE: 1

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Ala Leu Gly Ile Ser Tyr Gly
            35                  40                  45

Arg Lys Lys Arg Arg Gln Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu Xaa Lys Lys Lys Val Glu Arg Glu Thr Glu
                85                  90                  95

Thr Asp Pro Phe
            100

<210> SEQ ID NO 2
```

```
<211> LENGTH: 20
<212> TYPE: PRT
<213> ORGANISM: unknown
<220> FEATURE:
<223> OTHER INFORMATION: mammalian

<400> SEQUENCE: 2

Ala Cys Thr Asn Cys Tyr Cys Lys Lys Cys Cys Phe His Cys Gln Val
1               5                   10                  15

Cys Phe Ile Thr
            20

<210> SEQ ID NO 3
<211> LENGTH: 9
<212> TYPE: PRT
<213> ORGANISM: unknown
<220> FEATURE:
<223> OTHER INFORMATION: mammalian

<400> SEQUENCE: 3

Arg Lys Lys Arg Arg Gln Arg Arg Arg
1               5

<210> SEQ ID NO 4
<211> LENGTH: 100
<212> TYPE: PRT
<213> ORGANISM: unknown
<220> FEATURE:
<223> OTHER INFORMATION: mammalian
<220> FEATURE:
<221> NAME/KEY: MISC_FEATURE
<222> LOCATION: (87)..(87)
<223> OTHER INFORMATION: wherein the "Xaa" represents any amino acid

<400> SEQUENCE: 4

Met Glu Pro Val Asp Pro Arg Leu Glu Pro Trp Lys His Pro Gly Ser
1               5                   10                  15

Gln Pro Lys Thr Ala Ser Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu Xaa Lys Lys Lys Val Glu Arg Glu Thr Glu
                85                  90                  95

Thr Asp Pro Phe
            100

<210> SEQ ID NO 5
<211> LENGTH: 100
<212> TYPE: PRT
<213> ORGANISM: unknown
<220> FEATURE:
<223> OTHER INFORMATION: mammalian
<220> FEATURE:
<221> NAME/KEY: MISC_FEATURE
<222> LOCATION: (87)..(87)
<223> OTHER INFORMATION: wherein the "Xaa" represents any amino acid

<400> SEQUENCE: 5

Met Glu Pro Val Asp Pro Arg Leu Glu Pro Trp Lys His Pro Gly Ser
1               5                   10                  15

Gln Pro Lys Thr Ala Cys Thr Asn Ser Tyr Cys Lys Lys Cys Cys Phe
```

```
                20                  25                  30
His Cys Gln Val Cys Phe Ile Thr Lys Ala Leu Gly Ile Ser Tyr Gly
            35                  40                  45

Arg Lys Lys Arg Arg Gln Arg Arg Ala His Gln Asn Ser Gln Thr
        50                  55                  60

His Gln Ala Ser Leu Ser Lys Gln Pro Thr Ser Gln Pro Arg Gly Asp
 65                  70                  75                  80

Pro Thr Gly Pro Lys Glu Xaa Lys Lys Lys Val Glu Arg Glu Thr Glu
                85                  90                  95

Thr Asp Pro Phe
            100

<210> SEQ ID NO 6
<211> LENGTH: 100
<212> TYPE: PRT
<213> ORGANISM: unknown
<220> FEATURE:
<223> OTHER INFORMATION: mammalian
<220> FEATURE:
<221> NAME/KEY: MISC_FEATURE
<222> LOCATION: (87)..(87)
<223> OTHER INFORMATION: wherein the "Xaa" represents any amino acid

<400> SEQUENCE: 6

Met Glu Pro Val Asp Pro Arg Leu Glu Pro Trp Lys His Pro Gly Ser
 1               5                  10                  15

Gln Pro Lys Thr Ala Cys Thr Asn Cys Tyr Ser Lys Lys Cys Cys Phe
                20                  25                  30

His Cys Gln Val Cys Phe Ile Thr Lys Ala Leu Gly Ile Ser Tyr Gly
            35                  40                  45

Arg Lys Lys Arg Arg Gln Arg Arg Ala His Gln Asn Ser Gln Thr
        50                  55                  60

His Gln Ala Ser Leu Ser Lys Gln Pro Thr Ser Gln Pro Arg Gly Asp
 65                  70                  75                  80

Pro Thr Gly Pro Lys Glu Xaa Lys Lys Lys Val Glu Arg Glu Thr Glu
                85                  90                  95

Thr Asp Pro Phe
            100

<210> SEQ ID NO 7
<211> LENGTH: 100
<212> TYPE: PRT
<213> ORGANISM: unknown
<220> FEATURE:
<223> OTHER INFORMATION: mammalian
<220> FEATURE:
<221> NAME/KEY: MISC_FEATURE
<222> LOCATION: (87)..(87)
<223> OTHER INFORMATION: wherein the "Xaa" represents any amino acid

<400> SEQUENCE: 7

Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Ser Cys Phe
                20                  25                  30

His Cys Gln Val Cys Phe Ile Thr Lys Ala Leu Gly Ile Ser Tyr Gly
            35                  40                  45

Arg Lys Lys Arg Arg Gln Arg Arg Ala His Gln Asn Ser Gln Thr
        50                  55                  60

His Gln Ala Ser Leu Ser Lys Gln Pro Thr Ser Gln Pro Arg Gly Asp
 65                  70                  75                  80
```

```
Pro Thr Gly Pro Lys Glu Xaa Lys Lys Val Glu Arg Glu Thr Glu
                85                  90                  95

Thr Asp Pro Phe
            100

<210> SEQ ID NO 8
<211> LENGTH: 100
<212> TYPE: PRT
<213> ORGANISM: unknown
<220> FEATURE:
<223> OTHER INFORMATION: mammalian
<220> FEATURE:
<221> NAME/KEY: MISC_FEATURE
<222> LOCATION: (87)..(87)
<223> OTHER INFORMATION: wherein the "Xaa" represents any amino acid

<400> SEQUENCE: 8

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Ser Phe
                20                  25                  30

His Cys Gln Val Cys Phe Ile Thr Lys Ala Leu Gly Ile Ser Tyr Gly
            35                  40                  45

Arg Lys Lys Arg Arg Gln Arg Arg Ala His Gln Asn Ser Gln Thr
        50                  55                  60

His Gln Ala Ser Leu Ser Lys Gln Pro Thr Ser Gln Pro Arg Gly Asp
65                  70                  75                  80

Pro Thr Gly Pro Lys Glu Xaa Lys Lys Val Glu Arg Glu Thr Glu
                85                  90                  95

Thr Asp Pro Phe
            100

<210> SEQ ID NO 9
<211> LENGTH: 100
<212> TYPE: PRT
<213> ORGANISM: unknown
<220> FEATURE:
<223> OTHER INFORMATION: mammalian
<220> FEATURE:
<221> NAME/KEY: MISC_FEATURE
<222> LOCATION: (87)..(87)
<223> OTHER INFORMATION: wherein the "Xaa" represents any amino acid

<400> SEQUENCE: 9

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Ser Gln Val Cys Phe Ile Thr Lys Ala Leu Gly Ile Ser Tyr Gly
            35                  40                  45

Arg Lys Lys Arg Arg Gln Arg Arg Ala His Gln Asn Ser Gln Thr
        50                  55                  60

His Gln Ala Ser Leu Ser Lys Gln Pro Thr Ser Gln Pro Arg Gly Asp
65                  70                  75                  80

Pro Thr Gly Pro Lys Glu Xaa Lys Lys Val Glu Arg Glu Thr Glu
                85                  90                  95

Thr Asp Pro Phe
            100

<210> SEQ ID NO 10
<211> LENGTH: 100
```

-continued

```
<212> TYPE: PRT
<213> ORGANISM: unknown
<220> FEATURE:
<223> OTHER INFORMATION: mammalian
<220> FEATURE:
<221> NAME/KEY: MISC_FEATURE
<222> LOCATION: (87)..(87)
<223> OTHER INFORMATION: wherein the "Xaa" represents any amino acid

<400> SEQUENCE: 10

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Ser Gln Val Cys Phe Ile Thr Lys Ala Leu Gly Ile Ser Tyr Gly
        35                  40                  45

Arg Lys Lys Arg Arg Gln Arg Arg Ala His Gln Asn Ser Gln Thr
    50                  55                  60

His Gln Ala Ser Leu Ser Lys Gln Pro Thr Ser Gln Pro Arg Gly Asp
65                  70                  75                  80

Pro Thr Gly Pro Lys Glu Xaa Lys Lys Lys Val Glu Arg Glu Thr Glu
                85                  90                  95

Thr Asp Pro Phe
            100

<210> SEQ ID NO 11
<211> LENGTH: 20
<212> TYPE: PRT
<213> ORGANISM: unknown
<220> FEATURE:
<223> OTHER INFORMATION: mammalian
<220> FEATURE:
<221> NAME/KEY: MISC_FEATURE
<222> LOCATION: (1)..(1)
<223> OTHER INFORMATION: wherein the "Xaa" represents Ala
<220> FEATURE:
<221> NAME/KEY: MISC_FEATURE
<222> LOCATION: (2)..(2)
<223> OTHER INFORMATION: wherein the "Xaa" represents Cys or Ser
<220> FEATURE:
<221> NAME/KEY: MISC_FEATURE
<222> LOCATION: (3)..(3)
<223> OTHER INFORMATION: wherein the "Xaa" represents Thr
<220> FEATURE:
<221> NAME/KEY: MISC_FEATURE
<222> LOCATION: (4)..(4)
<223> OTHER INFORMATION: wherein the "Xaa" represents Asn
<220> FEATURE:
<221> NAME/KEY: MISC_FEATURE
<222> LOCATION: (5)..(5)
<223> OTHER INFORMATION: wherein the "Xaa" represents Cys or Ser
<220> FEATURE:
<221> NAME/KEY: MISC_FEATURE
<222> LOCATION: (6)..(6)
<223> OTHER INFORMATION: wherein the "Xaa" represents Tyr
<220> FEATURE:
<221> NAME/KEY: MISC_FEATURE
<222> LOCATION: (7)..(7)
<223> OTHER INFORMATION: wherein the "Xaa" represents Cys or Ser
<220> FEATURE:
<221> NAME/KEY: MISC_FEATURE
<222> LOCATION: (8)..(8)
<223> OTHER INFORMATION: wherein the "Xaa" represents Lys
<220> FEATURE:
<221> NAME/KEY: MISC_FEATURE
<222> LOCATION: (9)..(9)
<223> OTHER INFORMATION: wherein the "Xaa" represents Lys
<220> FEATURE:
<221> NAME/KEY: MISC_FEATURE
<222> LOCATION: (10)..(10)
<223> OTHER INFORMATION: wherein the "Xaa" represents Cys or Ser
<220> FEATURE:
```

<221> NAME/KEY: MISC_FEATURE
<222> LOCATION: (11)..(11)
<223> OTHER INFORMATION: wherein the "Xaa" represents Cys or Ser
<220> FEATURE:
<221> NAME/KEY: MISC_FEATURE
<222> LOCATION: (12)..(12)
<223> OTHER INFORMATION: wherein the "Xaa" represents Phe
<220> FEATURE:
<221> NAME/KEY: MISC_FEATURE
<222> LOCATION: (13)..(13)
<223> OTHER INFORMATION: wherein the "Xaa" represents His
<220> FEATURE:
<221> NAME/KEY: MISC_FEATURE
<222> LOCATION: (14)..(14)
<223> OTHER INFORMATION: wherein the "Xaa" represents Cys or Ser
<220> FEATURE:
<221> NAME/KEY: MISC_FEATURE
<222> LOCATION: (15)..(15)
<223> OTHER INFORMATION: wherein the "Xaa" represents Gln
<220> FEATURE:
<221> NAME/KEY: MISC_FEATURE
<222> LOCATION: (16)..(16)
<223> OTHER INFORMATION: wherein the "Xaa" represents Val
<220> FEATURE:
<221> NAME/KEY: MISC_FEATURE
<222> LOCATION: (17)..(17)
<223> OTHER INFORMATION: wherein the "Xaa" represents Cys or Ser
<220> FEATURE:
<221> NAME/KEY: MISC_FEATURE
<222> LOCATION: (18)..(18)
<223> OTHER INFORMATION: wherein the "Xaa" represents Phe
<220> FEATURE:
<221> NAME/KEY: MISC_FEATURE
<222> LOCATION: (19)..(19)
<223> OTHER INFORMATION: wherein the "Xaa" represents Ile
<220> FEATURE:
<221> NAME/KEY: MISC_FEATURE
<222> LOCATION: (20)..(20)
<223> OTHER INFORMATION: wherein the "Xaa" represents Thr

<400> SEQUENCE: 11

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20

<210> SEQ ID NO 12
<211> LENGTH: 20
<212> TYPE: PRT
<213> ORGANISM: unknown
<220> FEATURE:
<223> OTHER INFORMATION: mammalian
<220> FEATURE:
<221> NAME/KEY: MISC_FEATURE
<222> LOCATION: (1)..(1)
<223> OTHER INFORMATION: wherein the "Xaa" represents Ala
<220> FEATURE:
<221> NAME/KEY: MISC_FEATURE
<222> LOCATION: (2)..(2)
<223> OTHER INFORMATION: wherein the "Xaa" represents Cys
<220> FEATURE:
<221> NAME/KEY: MISC_FEATURE
<222> LOCATION: (3)..(3)
<223> OTHER INFORMATION: wherein the "Xaa" represents Thr
<220> FEATURE:
<221> NAME/KEY: MISC_FEATURE
<222> LOCATION: (4)..(4)
<223> OTHER INFORMATION: wherein the "Xaa" represents Asn
<220> FEATURE:
<221> NAME/KEY: MISC_FEATURE
<222> LOCATION: (5)..(5)
<223> OTHER INFORMATION: wherein the "Xaa" represents Cys
<220> FEATURE:
<221> NAME/KEY: MISC_FEATURE
<222> LOCATION: (6)..(6)
<223> OTHER INFORMATION: wherein the "Xaa" represents Tyr
<220> FEATURE:

```
<221> NAME/KEY: MISC_FEATURE
<222> LOCATION: (7)..(7)
<223> OTHER INFORMATION: wherein the "Xaa" represents Cys
<220> FEATURE:
<221> NAME/KEY: MISC_FEATURE
<222> LOCATION: (8)..(8)
<223> OTHER INFORMATION: wherein the "Xaa" represents Lys
<220> FEATURE:
<221> NAME/KEY: MISC_FEATURE
<222> LOCATION: (9)..(9)
<223> OTHER INFORMATION: wherein the "Xaa" represents Lys
<220> FEATURE:
<221> NAME/KEY: MISC_FEATURE
<222> LOCATION: (10)..(10)
<223> OTHER INFORMATION: wherein the "Xaa" represents Cys
<220> FEATURE:
<221> NAME/KEY: MISC_FEATURE
<222> LOCATION: (11)..(11)
<223> OTHER INFORMATION: wherein the "Xaa" represents Cys
<220> FEATURE:
<221> NAME/KEY: MISC_FEATURE
<222> LOCATION: (12)..(12)
<223> OTHER INFORMATION: wherein the "Xaa" represents Phe
<220> FEATURE:
<221> NAME/KEY: MISC_FEATURE
<222> LOCATION: (13)..(13)
<223> OTHER INFORMATION: wherein the "Xaa" represents His
<220> FEATURE:
<221> NAME/KEY: MISC_FEATURE
<222> LOCATION: (14)..(14)
<223> OTHER INFORMATION: wherein the "Xaa" represents Cys
<220> FEATURE:
<221> NAME/KEY: MISC_FEATURE
<222> LOCATION: (15)..(15)
<223> OTHER INFORMATION: wherein the "Xaa" represents Gln
<220> FEATURE:
<221> NAME/KEY: MISC_FEATURE
<222> LOCATION: (16)..(16)
<223> OTHER INFORMATION: wherein the "Xaa" represents Val
<220> FEATURE:
<221> NAME/KEY: MISC_FEATURE
<222> LOCATION: (17)..(17)
<223> OTHER INFORMATION: wherein the "Xaa" represents Cys
<220> FEATURE:
<221> NAME/KEY: MISC_FEATURE
<222> LOCATION: (18)..(18)
<223> OTHER INFORMATION: wherein the "Xaa" represents Phe
<220> FEATURE:
<221> NAME/KEY: MISC_FEATURE
<222> LOCATION: (19)..(19)
<223> OTHER INFORMATION: wherein the "Xaa" represents Ile
<220> FEATURE:
<221> NAME/KEY: MISC_FEATURE
<222> LOCATION: (20)..(20)
<223> OTHER INFORMATION: wherein the "Xaa" represents Thr

<400> SEQUENCE: 12

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20
```